US012121650B2

(12) United States Patent
Muellinger et al.

(10) Patent No.: US 12,121,650 B2
(45) Date of Patent: Oct. 22, 2024

(54) PHARMACEUTICAL ADMINISTRATION TO NEONATES, INFANTS AND CHILDREN

(71) Applicant: Vectura Delivery Devices Limited, Chippenham (GB)

(72) Inventors: Bernhard Muellinger, Gauting (DE); Susan Snape, Cambridge (GB)

(73) Assignee: Vectura Delivery Devices Limited, Chippenham Wiltshire (GB)

(*) Notice: Subject to any disclaimer, the term of this patent is extended or adjusted under 35 U.S.C. 154(b) by 615 days.

(21) Appl. No.: 17/283,669

(22) PCT Filed: Oct. 16, 2019

(86) PCT No.: PCT/EP2019/078048
§ 371 (c)(1),
(2) Date: Apr. 8, 2021

(87) PCT Pub. No.: WO2020/079055
PCT Pub. Date: Apr. 23, 2020

(65) Prior Publication Data
US 2022/0008666 A1 Jan. 13, 2022

(30) Foreign Application Priority Data
Oct. 19, 2018 (EP) .................................... 18201606

(51) Int. Cl.
*A61M 11/02* (2006.01)
*A61K 9/00* (2006.01)
(Continued)

(52) U.S. Cl.
CPC ........... *A61M 11/02* (2013.01); *A61K 9/0078* (2013.01); *A61K 31/569* (2013.01);
(Continued)

(58) Field of Classification Search
CPC .. A61K 9/0078; A61K 31/569; A61K 31/573; A61K 31/58; A61M 11/02;
(Continued)

(56) References Cited

U.S. PATENT DOCUMENTS

| | | | |
|---|---|---|---|
| 6,606,989 | B1 | 8/2003 | Brand et al. |
| 8,668,901 | B2 | 3/2014 | Muellinger et al. |

(Continued)

FOREIGN PATENT DOCUMENTS

WO WO 2011/038901 A1 4/2011

OTHER PUBLICATIONS

International Search Report for International Application No. PCT/EP2019/078048, Dec. 16, 2019.

(Continued)

*Primary Examiner* — Joshua Lee
(74) *Attorney, Agent, or Firm* — FINNEGAN, HENDERSON, FARABOW, GARRETT & DUNNER LLP

(57) ABSTRACT

The invention provides methods, devices and compositions for use in inhalation therapy of neonates, infants or children younger than 12 years, e.g. from 1 to 8 years, suffering from a disease, optionally a pulmonary disease, such as asthma, by which high amounts of inhaled drugs are directed to the small airways of the peripheral lungs of neonates, infants and children using slow, controlled flow rates and pre-set inhalation volumes. A novel inhalation device tailored for use in neonates, infants and children and adapted to provide said slow, controlled flow rates with a simplified jet nebuliser set-up is disclosed, together with kits comprising the device.

8 Claims, 2 Drawing Sheets

(51) Int. Cl.

| | |
|---|---|
| ***A61K 31/569*** | (2006.01) |
| ***A61K 31/573*** | (2006.01) |
| ***A61K 31/58*** | (2006.01) |
| *A61M 16/06* | (2006.01) |
| *A61M 16/20* | (2006.01) |

(52) U.S. Cl.
CPC ............ *A61K 31/573* (2013.01); *A61K 31/58* (2013.01); *A61M 16/06* (2013.01); *A61M 16/208* (2013.01); *A61M 2240/00* (2013.01)

(58) Field of Classification Search
CPC .. A61M 11/06; A61M 16/06; A61M 16/0816; A61M 16/20; A61M 16/208; A61M 2016/0018; A61M 2016/0027; A61M 2205/50; A61M 2240/00
See application file for complete search history.

(56) References Cited

U.S. PATENT DOCUMENTS

| | | | | |
|---|---|---|---|---|
| 8,834,848 | B2 | 9/2014 | Muellinger et al. | |
| 2010/0092397 | A1* | 4/2010 | Hofmann ................ | A61P 43/00 424/43 |
| 2013/0034534 | A1* | 2/2013 | Kroneberg .............. | A61P 43/00 424/94.6 |
| 2017/0304565 | A1* | 10/2017 | Allosery ........... | A61M 15/0091 |
| 2018/0333159 | A1* | 11/2018 | Smith .................. | A61B 17/132 |

OTHER PUBLICATIONS

Written Opinion of the International Searching Authority for International Application No. PCT/EP2019/078048.

* cited by examiner

PHARMACEUTICAL ADMINISTRATION TO NEONATES, INFANTS AND CHILDREN

FIELD

The application is a national stage filing under 35 U.S.C. § 371 of International Application No. PCT/EP2019/078048, filed on Oct. 16, 2019, which claims priority of European Patent Application No. 18201606.3, filed Oct. 19, 2018. The contents of these applications are each incorporated herein by reference.

The present invention relates to methods, devices and compositions for use in the therapy of neonates, infants or children younger than 12 years, e.g. from 1 to 8 years, who are suffering from a disease, optionally a pulmonary disease such as asthma, by which high amounts of inhaled drugs are directed to the small airways of the peripheral lungs of neonates, infants and children.

BACKGROUND

The application of inhalation drugs, such as corticosteroids or anti-infectives, in neonates, infants and young children is often problematic for a variety of reasons, such as children's narrower airways, higher distress when experiencing shortness of breath, or lower ability to follow verbal instructions on how best to inhale. Also, children often exhibit fast but shallow breathing patterns, and many inhalation devices are not customised for children in terms of optimising said breathing patterns, resulting in inefficient lung delivery. Therefore, inhalation in neonates, infants and young children is often associated with long treatment times, low compliance to dosing and inhalation technique and distinct variabilities in breathing pattern (inhalation flow rates, inhalation volumes), which directly influence the delivered doses inhaled by the patient. Thus, this negatively impacts deposition patterns and deposition efficiencies in the regional and especially in the small airways.

Furthermore, the majority of children are not able to properly inhale via a mouthpiece with dry powder inhalers (DPI), metered dose inhalers (MDI) with spacers or with conventional nebulisers. Therefore, facemasks are typically used in children aged 1 to 4 years, and often up to adolescence, although it is well known that facemasks are associated with a low deposition efficiency of the inhaled aerosol in the lung and also a high deposition of inhaled aerosol in the upper airways. Most facemasks available provide suboptimal sealing to the patients face. Specifically, during inspiration this often leads to the effect that during inhalation mostly room air is inhaled. When using nebulisers this often causes a critical use error, which often leads to a dramatic reduction of the dose delivered to the patient and, in some cases, administration of no drug at all. Inefficient delivery via facemasks is partly due to children inhaling predominantly through the nose when using facemasks. The nasal airways are both narrower and longer compared to oral inhalation, increasing the fraction of inhaled particles lost by impaction in the nasal airways. Nasally inhaled particles or droplets may be held back further by the cilial lining in the nasal airways.

Even if the neonate, infant or child inhales through the mouth, quite a high fraction of the administered active agent, or drug, is deposited in the oropharynx (i.e. the throat- or mouth region) rather than the lungs when using conventional nebulisers; for instance, about 60% with conventional jet nebulisers. This 'mis-delivered' drug fraction then either gets swallowed, thereby increasing the risk of systemic side effects, and/or it causes local side effects in the throat. For instance, in case of corticosteroids, systemic side effects include weight gain, changes in behaviour, growth retention, irritation of the stomach lining; and local side effects include hoarseness, voice alteration, loss of voice, laryngitis or pharyngeal thrush (also called candidiasis).

Also, due to inefficient delivery of the active agents, higher doses must be administered; often, the same or similar doses as used for adults. This does not only increase the risk of local and/or systemic side effects further, but also renders inhalation treatments more time intensive; for instance, it takes about 5 minutes to nebulise a complete fill dose of a 2 mL budesonide vial. Depending on the formulation and dose to be inhaled, the pause times required by the child and the selection of the nebuliser, this time may easily increase up to 40 minutes.

In addition, delivery of nebulised drug suspensions, such as corticosteroid suspensions, is particularly difficult since the droplet size achieved when nebulising suspensions is not ideal for treatment of children. For an efficient delivery in children, a droplet size of about 3 μm would be ideal in order to target the corticosteroids to the small airways where their mode-of-action is. However, suspensions, when nebulised, are causing a rise of the mass median aerodynamic diameter (MMAD) of the nebulised particles or droplets; usually the droplet size of suspensions, such as inhalable budesonide suspensions, is raised by about 1 μm compared to inhalation solutions. With most conventional nebulisers, the droplet size of suspensions is raised to above 5 μm. In neonates, infants and children this increased droplet size causes high deposition in the upper airways, when patients inhale with normal inspiratory flow rates.

U.S. Pat. No. 8,668,901 B2 describes the administration of corticosteroids such as budesonide to adults and children older than 12 years, using an inhalation-triggered device providing controlled inhalation flow rates and volumes; i.e. in a way the patient is given artificial respiration since the inhalation device sets and adjusts the respiratory flow. For instance, the nebulised aerosol may be administered during the inhalation phase of the patient at a rate of not more than about 20 L/min and at a total inhaled gas phase volume of at least about 0.4 L per inhalation, preferably at a flow rate of 12 L/min and a total inhaled volume of 0.4 to 1.4 L. This controlled inhalation is said to provide for increased deposition of the inhalable corticosteroids in the small airways of the peripheral lungs, and in consequence a reduction in corticosteroid-related adverse effects as well as a substantial decrease in the dose of concurrently required oral corticosteroids (e.g. prednisone, prednisolone, methyl-prednisone, dexamethasone or hydrocortisone).

One of the devices suggested for administering corticosteroids by controlled inhalation is described in U.S. Pat. No. 6,606,989 B1 which describes a device consisting of an inhalation mouthpiece with an associated adjustable nebuliser and a compressed-air control valve through which a pre-settable volumetric flow of compressed air can be discharged from a separate compressed-air supply to the nebuliser containing a liquid composition throughout a settable period of time. For operation of the device an electronic controller is provided by which the nebulising period of the nebuliser and a pause interval can be set. In addition, the device is triggering the beginning of the nebulising operation by means of a pressure sensor responsive to a suction pressure in, or at, the mouthpiece.

The documents are silent, though, on inhalation regimens for neonates, infants and younger children, in particular neonates, infants or children younger than 12 years, or from e.g. 1 to 8 years.

It is thus an object of the present invention to provide improved methods for administering inhalable pharmaceutical compositions to neonates, infants or children younger than 12 years, or from 1 to 8 years, who are suffering from disease, optionally a pulmonary disease, in such a way that the above-mentioned drawbacks known from prior art are overcome; e.g. the inefficient and variable deposition in the peripheral lungs, the local or systemic side effects by excess and/or 'mis-delivered' drug, or the lengthy treatment times. It is a further object to provide an inhalation device for this purpose, or in other words an inhalation device adapted for use with or by neonates, infants and young children (herein also referred to as a paediatric inhalation device), preferably with a simpler functional design or construction than prior art devices.

SUMMARY OF THE INVENTION

In a first aspect, the invention provides a method of treatment of a subject being a neonate, infant or child younger than 12 years suffering from a disease, optionally a pulmonary disease, which comprises administering to said subject a composition as an aerosol via a mouthpiece or a facemask, wherein said aerosol is comprised in a gas phase, and wherein said gas phase is administered to said subject:

(a) at a flow rate of from about 4 L/min to about 9 L/min during the inhalation period of the subject, and (b) at a total volume of about 0.10 L to 0.80 L per inhalation.

In a second aspect, the invention provides an inhalation device adapted to emit an inhalable pharmaceutical composition in the form of an aerosol comprised in a gas phase, the inhalation device comprising:

(i) an inhalation interface for providing the emitted aerosol in the gas phase to the airways of a subject, (ii) a jet nebuliser associated with the inhalation interface for generating the aerosol, (iii) an electronically controlled compressor for providing a flow of gas phase to said jet nebuliser, (iv) an electronic controller, wherein the electronic controller is adapted to directly control the operation of the electronically controlled compressor, and wherein the inhalation device is adapted to provide the complete gas phase comprising the aerosol through the nozzle of the jet nebuliser.

In a third aspect, the invention provides a kit comprising the inhalation device according to second aspect of the invention together with an inhalable pharmaceutical composition; optionally a pharmaceutical inhalation suspension or solution, further optionally a pharmaceutical inhalation suspension or solution comprising a glucocorticoid such as budesonide, fluticasone, beclomethasone, mometasone; or a short acting bronchodilator (SABA) such as salbutamol, fenoterol, levosalbutamol, procaterol, terbutaline, pirbuterol, orciprenaline, isoprenaline, biloterol.

In a fourth aspect, the invention provides the use of the inhalation device according to the second aspect of the invention, or the kit according to the third aspect of the invention in the therapy of a subject suffering from a disease, optionally a pulmonary disease.

Definitions

The following terms or expressions as used herein should normally be interpreted as outlined in this section, unless defined otherwise by the description or unless the specific context indicates or requires otherwise:

All technical terms as used herein shall be understood to have the same meaning as is commonly understood by a person skilled in the relevant technical field.

The words 'comprise', 'comprises' and 'comprising' and similar expressions are to be construed in an open and inclusive sense, as 'including, but not limited to' in this description and in the claims.

The singular forms 'a', 'an' and 'the' should be understood as to include plural referents. In other words, all references to singular characteristics or limitations of the present disclosure shall include the corresponding plural characteristic or limitation, and vice versa. The terms 'a' 'an' and 'the' hence have the same meaning as 'at least one' or as 'one or more'. For example, reference to 'an ingredient' includes mixtures of ingredients, and the like.

The expressions, 'one embodiment', 'an embodiment', 'a specific embodiment' and the like mean that a particular feature, property or characteristic, or a particular group or combination of features, properties or characteristics, as referred to in combination with the respective expression, is present in at least one of the embodiments of the invention. These expressions, occurring in various places throughout this description, do not necessarily refer to the same embodiment. Moreover, the particular features, properties or characteristics may be combined in any suitable manner in one or more embodiments.

The expression 'and/or' (e.g. as in "A and/or B") shall mean the same as "A or B, or both A and B".

All percentages, parts and/or ratios in the context of numbers should be understood as relative to the total number of the respective items, unless otherwise specified, or indicated or required by the context. Furthermore, all percentages parts and/or ratios are intended to be by weight of the total weight; e.g. '%' should be read as 'wt.-%', unless otherwise specified, or indicated or required by the context.

'Essentially', 'about', 'approximately' (approx.), 'circa' (ca.) and the like in connection with an attribute or value include the exact attribute or the precise value, as well as any attribute or value typically considered to fall within a normal range or variability accepted in the technical field concerned.

The term 'aerosol' refers to solid or semisolid particles, or liquid droplets which are dispersed in a gas phase, such as air; i.e. the gas phase comprises the aerosol. The term 'nebulised aerosol' in particular refers to an aerosolised liquid; i.e. droplets of liquid dispersed in a gas phase, typically with a particle size distribution, or more specifically a droplet size distribution, which is suitable for inhalation therapy. The term 'nascent aerosol' refers more specifically to the freshly prepared and dense aerosol as expelled from the aerosol generator which then is diluted with a gas phase such as air prior to being inhaled by a user of the inhalation device. In analogy, the term 'a nascent aerosol outlet' refers to the position in the inhalation device where the nascent aerosol is expelled from the aerosol generator and into the gas stream inhaled by the user; for instance, in a device comprising a jet nebuliser, the nascent aerosol outlet would be positioned at the nozzle of the jet nebuliser.

The term 'inhalation interface' as used herein refers to the component of the inhalation device by which a user receives the aerosol produced by the inhalation device. The inhalation interface typically comprises the actual aerosol generator (such as a jet nebuliser or a vibrating mesh nebuliser), a reservoir for filling in the pharmaceutical composition to be aerosolised and an aerosol outlet opening in the form of, for instance, a mouthpiece or a facemask. Instead of a fillable reservoir, or in addition thereto, the inhalation interface may comprise a flange or other attachment point for attaching a separate reservoir such as a drug suspension filled cartridge or the like. Optionally, the inhalation interface may further comprise a spacer; although in the majority of cases a spacer will not be required with the inhalation method and device of the invention. Commonly the inhalation interface is a light-weight, hand-held 'handset'—attached via flexible tubing to the inhalation device's main body, or base unit (typically, a table-top device unit, housing most of the electronics and the compressor, for instance) and held by the user during use—combined with either a mouthpiece or a facemask.

The term 'jet nebuliser' as used herein refers to the actual nebulising component of an inhalation device associated with the inhalation interface (e.g. positioned in the central bottom portion of the handset) which operates by passing a compressed gas, such as air or oxygen, through a venturi nozzle and from there at high velocity through a liquid medicine to turn it into an aerosol.

The term 'vibrating mesh nebuliser' as used herein refers to the actual nebulising component of an inhalation device associated with the inhalation interface which operates by rapidly vibrating a perforated mesh, or membrane, with several thousands of minute holes in direct contact with a liquid composition in a reservoir, and thereby pressing, or forcing, the liquid through the holes in the form of a mist of very fine, inhalable aerosol droplets.

The term 'static dead volume' ($DV_s$) refers to the volume defined by the actual physical dimensions of the inhalation interface between the nascent aerosol outlet at the upstream end of the inhalation interface and the outlet opening at the downstream end of the inhalation interface facing the subject's mouth. The term 'static dead space' may be used synonymously.

The term 'virtual dead volume ($DV_v$)' refers to the volume fraction of the static dead volume ($DV_s$) which—during use of the inhalation device—does not remain filled with aerosol-comprising gas phase; for instance, because the subject exhales into the inhalation device, or the inhalation interface (thereby 'pushing back' the column of aerosol-comprising gas phase into the device); and/or because of partial losses of the aerosol-comprising gas phase into ambient air while the inhalation interface is moved away from the subject's face or mouth and the aerosol outlet opening is uncovered (e.g. during exhalation). Both result in a virtual dead volume of aerosol-free, or almost aerosol-free, gas phase which then has to be inhaled first during the next inhalation.

The term 'breath-actuated' refers to a device or device component whose onset of operation is linked with a sensed breathing manoeuvre, for instance, commencing operation upon a sensed inhalation. The term is thus used synonymously herein with the term 'inhalation-triggered'. The respective signal, or trigger, may for instance, be derived from a pressure sensor responsive to the suction pressure created by inhaling.

The term 'filling volume' refers to the volume of a composition filled into the nebulizer (e.g. filled into a dedicated compartment in the handset).

The expressions 'inhalable corticosteroid' or 'inhalable glucocorticoid' refer to a corticosteroid or glucocorticoid, respectively, that is suitable for delivery by inhalation, including but not limited to e.g. fluticasone, beclomethasone, budesonide, mometasone, ciclesonide, flunisolide, or triamcinolone. In that regard, the name of any drug should be understood so as to include any pharmaceutically useful salts, solvates and physical forms; e.g. 'fluticasone' is understood as including fluticasone propionate and fluticasone furoate. Other salts of interest include beclomethasone dipropionate, mometasone furoate, and triamcinolone acetonide.

The expressions 'inhalable short acting bronchodilator' or 'inhalable SABA' refer to a short acting bronchodilator that is suitable for delivery by inhalation, including but not limited to a short acting bronchodilator such as salbutamol, fenoterol, levosalbutamol, procaterol, terbutaline, pirbuterol, orciprenaline, isoprenaline, biloterol.

The expressions 'peripheral lungs' or 'lower lungs', 'deep lungs' or 'small airways' refer to an area of the lungs primarily containing alveoli and bronchioles, which is a primary site of e.g. asthmatic inflammation, narrowing and constriction. High and selective deposition of many drugs in this area, including inhalable corticosteroid, is eminently desirable and contribute to an efficacious treatment of many pulmonary diseases, including asthma.

The expressions 'central lungs' or 'upper lungs' or 'larger airways' on the other hand refer to the area of lungs containing bronchi and trachea, i.e. being situated closer to the mouth. The 'oropharyngeal area', 'oropharynx' or 'extra-thoracic area' means the oral cavity, nasal cavity, throat, pharynx and larynx. In case of corticoid administration, it is preferred that there is only limited deposition in these regions.

The term 'one breath', or 'a breath' means a period of time when a person inhales and exhales during a regular breathing pattern that includes inhaling and exhaling. 'Inspiration' or 'inhalation' means the fraction of one breath when a person inhales. Likewise, 'expiration' or 'exhalation' refers to the fraction of one breath when a person exhales.

The term 'portable' as used herein refers to products or devices, in particular to inhalation devices, whose size and weight renders them suitable to be carried comfortably and for extended periods of time (such as the whole day and/or on a daily basis) by human users of said product without additional help; for instance, by simply holding it in one hand or by placing it in the pockets of trousers or coats or in a handbag or a backpack and/or a dedicated case. The term includes both handheld, pocket-sized inhalation devices as well as table-top devices, but excludes stationary devices (e.g. devices which cannot be carried comfortably due to being in-built, or fixed to, larger structures and/or simply being too heavy to be carried by a human user). Typically, products with a size of about 30×25×20 cm or smaller and an overall weight of less than 4 kg or preferably less than 3 kg (including at least the parts required for the device to be fully operational) are considered portable in the sense of the present invention. The term 'portable' further means that, in order for the device to be fully operational, nothing more than an electrical power source is needed (i.e. a socket to plug the device in); for instance, no external pressurised gas source is needed to provide air flow.

The expression '0 year to x year(s)' refers to any age between birth and the age of x years; for instance, '0 year' could refer to a neonate of only a few minutes or hours of age as well as to any age up to the infant's first birthday.

Any reference signs in the claims should not be construed as a limitation to the embodiments represented in any of the drawings.

BRIEF DESCRIPTION OF THE FIGURES

FIG. 3A shows the simplest embodiment, and FIG. 3B shows one of the preferred embodiments.

DETAILED DESCRIPTION OF THE INVENTION

Figure 1:
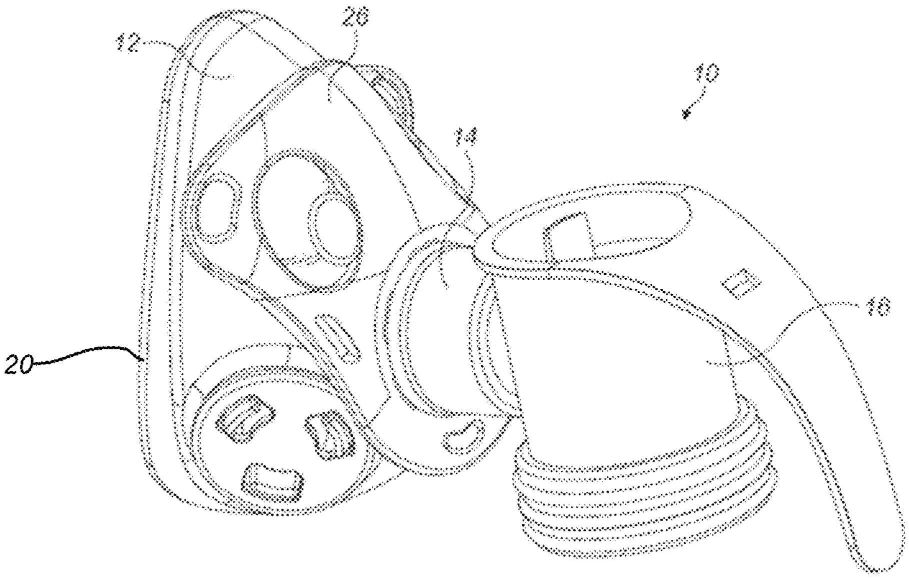
FIG. 1 shows a facemask suitable for use with the inhalation device according to the second aspect of the invention.

In a first aspect, the invention provides a method of treatment of a subject being a neonate, infant or child younger than 12 years suffering from a disease, optionally a pulmonary disease, which comprises administering to said subject a composition as an aerosol via a mouthpiece or a facemask, wherein said aerosol is comprised in a gas phase, and wherein said gas phase is administered to said subject:

(a) at a flow rate of from about 4 L/min to about 9 L/min during the inhalation period of the subject, (b) at a total volume of about 0.10 L to about 0.80 L per inhalation, and (c) wherein the gas phase comprising the aerosol is administered via an inhalation interface exhibiting a static dead volume ($DV_s$) between a nascent aerosol outlet at the upstream end of the inhalation interface and an outlet opening at the downstream end of the inhalation interface facing the subject's mouth of not more than 150 ml.

In other words, according to a first aspect, the invention provides a method of administering an inhalable pharmaceutical composition as an aerosol to a neonate, infant or child younger than 12 years, or from 1 to 8 years, which is suffering from a disease, optionally a pulmonary disease, wherein said method comprises the steps of administering the aerosol in form of a gas phase comprising the aerosol to said neonate, infant or child (a) at a flow rate of from about 4 L/min to about 9 L/min during the inhalation period of the neonate, infant or child, and (b) at a total volume of about 0.10 L to 0.80 L per inhalation.

In one embodiment, the subject to whom the inhalable pharmaceutical composition is administered as an aerosol is a neonate, an infant or a child aged 0 year to 11 years; or 1 hour to 11 years; or 0.5 year to 11 years; or 1 year to 11 years; or 1 year to 10 years; or 1 year to 9 years; 1 year to 8 years; or 1 year to 7 years; or 1 year to 6 years; or 1 year to 5 years; or 1 year to 4 years; or 1 year to 3 years; or 1 year to 2 years.

It has been surprisingly found by the inventors that by selecting inhalation parameters in the ranges according to the first aspect of the invention (i.e. flow rate between about 4 L/min and about 9 L/min during the inhalation period and a total volume of about 0.10 L to 0.80 L administered per inhalation) and providing such slow, constant flow during the neonate's, infant's or child's inspiration, deposition of larger fractions of drug in the deep lungs was successfully achieved, or in other words, less drug was deposited unfavourably in the central lungs, also referred as the upper lungs. Thereby, not only the risk and extent of side effects (such as weight gain, growth retention, irritation of the stomach lining, hoarseness, laryngitis or pharyngeal thrush) can be decreased advantageously but also the time required to administer a specific target dose to the deep lungs, as well as the amount of pharmaceutical composition needed in excess of this target dose are decreased. For instance, with inhalable budesonide suspensions, the inventors found that the delivered dose could be reduced by a factor of about 2.6 while still achieving the same target dose range in the peripheral lungs, or lower lungs or small airways where budesonide and other corticosteroids should preferably be deposited to achieve the best efficacy (see e.g. Example 2).

The inventors also found that by using slow inhalation flow rates (e.g. 6 L/min) a further reduction of treatment time can be achieved (i.e. beyond the reduction caused by more efficient deep lug delivery) since these slow inhalation flow rates also cause a change of the so-called I:E ratio (inhalation: exhalation ratio); for instance, reducing the usual 1:1.5 ratio obtained during tidal breathing to about 1:1 at controlled breathing with a flow rate of 6 L/min during inhalation. In other words, the expiratory time during inhalation treatments with such low flow rates is reduced, causing a reduction of the total treatment time by about 30%. In total, the authors found that treatment times could be reduced significantly (e.g. from about 5-8 min with conventional nebulisers to about 2-3 minutes), in some cases reduced by more than a factor of 3.

Further embodiments and preferred embodiments will be described below.

Typically, the gas phase comprising the aerosol is generated by an inhalation device. In one embodiment, the inhalable pharmaceutical composition may be administered by an inhalation device which is adapted to ($a_1$) emit the gas phase comprising the aerosol during the inhalation period of the subject at a flow rate of from about 4 L/min to about 9 L/min, or from about 4.8 L/min to about 7.2 L/min, or from about 5.5 L/min to about 7.5 L/min, and ($b_1$) emit, per inhalation, a total volume of about 0.10 L to about 0.80 L of the gas phase.

It should be understood that while it is theoretically possible to also administer, or emit, the gas phase comprising the aerosol during the exhalation period, this is usually not advisable, since it leads to unfavourable losses of the inhalable pharmaceutical composition (drug that is clearly not reaching the lungs) as well as potential contamination of the ambient air in the room where the composition is administered. This in turn could result in negative side effects not only for the neonate, infant or child but also other persons in this room, such as the parents, caregivers, siblings, or the like. Therefore, in one of the preferred aspects of the invention's first aspect, the gas phase comprising the aerosol is administered at a flow rate of from about 4 L/min to about 9 L/min, or from about 4.8 L/min to about 7.2 L/min, or from about 5.5 L/min to about 7.5 L/min, only during the inhalation period of the neonate, infant or child, whereas no gas phase, and in particular no gas phase comprising aerosol, is administered during the exhalation phase. Alternatively, the gas phase comprising the aerosol may be administered at a flow rate of from about 4 L/min to about 9 L/min, or from about 4.8 L/min to about 7.2 L/min, or from about 5.5 L/min to about 7.5 L/min, during the inhalation period of the neonate, infant or child, whereas a far lower flowrate of below 2 L/min, preferably below 1 L/min is used during the exhalation phase; e.g. about 0.8 L/min or about 0.5 L/min.

In exemplary embodiments, the gas phase comprising the aerosol is administered during the inhalation period of the subject at a flow rate in the range of from about 4.0 L/min to about 8.5 L/min; or from about 4.5 L/min to about 8.5 L/min; or from about 4.5 L/min to about 8.0 L/min; or from about 4.8 L/min to about 7.2 L/min; or from about 5.0 L/min to about 8.0 L/min; or from about 5.0 L/min to about 7.5 L/min; or from about 5.5 L/min to about 7.5 L/min; or from about 5.5 L/min to about 7.0 L/min; or from about 6.0 L/min to about 7.0 L/min; or from about 6.0 L/min to about 6.5

L/min; for instance, at a flow rate of about 4 L/min; or about 4.5 L/min; or about 5 L/min; or about 5.5 L/min; or about 6 L/min; or about 6.5 L/min; or about 7 L/min; or about 7.5 L/min; or about 8 L/min; or about 8.5 L/min; or about 9 L/min. In one of the preferred embodiments, the gas phase comprising the aerosol is administered during the inhalation period of the subject at a flow rate in the range of from about 4.8 L/min to about 7.2 L/min. In a further preferred embodiment, the flow rate is about 6 L/min.

In further exemplary embodiments, the total volume of gas phase administered per inhalation phase is in the range of from about 0.15 L to about 0.80 L; from about 0.20 L to about 0.80 L; or from about 0.20 L to about 0.75 L; or from about 0.25 L to about 0.75 L; or from about 0.25 L to about 0.70 L; or from about 0.30 L to about 0.80 L; or from about 0.30 L to about 0.70 L; or from about 0.30 L to about 0.65 L; or from about 0.35 L to about 0.65 L; or from about 0.35 L to about 0.6 L; or from about 0.40 L to about 0.60 L; or from about 0.40 L to about 0.55 L; or from about 0.45 L to about 0.55 L; or from about 0.45 L to about 0.50 L; or from about 0.10 L to about 0.30 L; or from about 0.10 L to about 0.25 L; or from about 0.10 L to about 0.20 L; or from about 0.10 L to about 0.15 L; or from about 0.15 L to about 0.30 L; or from about 0.15 L to about 0.25 L; or from about 0.15 L to about 0.20 L; or from about 0.20 L to about 0.30 L; or from about 0.25 L to about 0.30 L; or from about 0.30 L to about 0.50 L; or from about 0.30 L to about 0.45 L; or from about 0.30 L to about 0.40 L; or from about 0.30 L to about 0.35 L; or from about 0.35 L to about 0.50 L; or from about 0.35 L to about 0.45 L; or from about 0.35 L to about 0.40 L; or from about 0.40 L to about 0.50 L; or from about 0.45 L to about 0.50 L; or from about 0.40 L to about 0.80 L; or from about 0.45 L to about 0.80 L; or from about 0.50 L to about 0.80 L; or from about 0.55 L to about 0.80 L; or from about 0.60 L to about 0.80 L; or from about 0.65 L to about 0.80 L; or from about 0.70 L to about 0.80 L; or from about 0.75 L to about 0.80 L; or from about 0.40 L to about 0.75 L; or from about 0.45 L to about 0.75 L; or from about 0.50 L to about 0.75 L; or from about 0.55 L to about 0.75 L; or from about 0.60 L to about 0.75 L; or from about 0.65 L to about 0.75 L; or from about 0.70 L to about 0.75 L; or from about 0.40 L to about 0.70 L; or from about 0.45 L to about 0.70 L; or from about 0.50 L to about 0.70 L; or from about 0.55 L to about 0.70 L; or from about 0.60 L to about 0.70 L; or from about 0.65 L to about 0.70 L; or from about 0.40 L to about 0.60 L; or from about 0.45 L to about 0.60 L; or from about 0.50 L to about 0.60 L; or from about 0.55 L to about 0.60 L; for instance, about 0.10 L; or about 0.15 L; or about 0.20 L; or about 0.25 L; or about 0.30 L; or about 0.35 L; or about 0.40 L; or about 0.45 L; or about 0.50 L; or about 0.55 L; or about 0.60 L; or about 0.65 L; about 0.70 L; or about 0.75 L; or about 0.80 L. In one of the preferred embodiments, the total volume of gas phase administered per inhalation phase is in the range of from about 0.4 L to about 0.8 L. In one of the further preferred embodiments, the total volume of gas phase administered per inhalation phase is in the range of from about 0.6 L to about 0.8 L.

It should further be understood that within the ranges provided above, the flow rate and volume per inhalation may be selected to have any value, and said values may be pre-set by, or with, the inhalation device. In particular, the volume administered per inhalation can be selected freely; preferably based on how much the neonate, infant or child can inhale comfortably during a deep yet unstrained inhalation. Naturally, smaller inhalation volumes are more suited for younger children; e.g. a volume of 0.20 L may be suited mainly for neonates, infants and children aged 1 to 2 years; a volume of 0.40 L mainly for neonates, infants and children aged 3 to 5 years; or a volume of 0.80 L mainly for neonates, infants and children aged 6 to 8 years or 6 to 12 years. However, this is just a very basic guideline since, commonly, the appropriate inhalation volume is less ruled by the age of the child but rather by its height and bodyweight. Also, children with distinct pulmonary obstructions may initially require smaller inhalation volumes than children of identical age with less obstructions, but then increase said volume over time and in response to successful deep lung delivery of the inhalable pharmaceutical composition. A first guidance on the selection of initial inhalation volumes is provided in Table 1 below; if the neonate, infant or child cannot inhale the proposed volume comfortably, adaptions may be made.

Table 1: Guidance on selection of initial inhalation volumes (as well as the numbers of breaths and estimated treatment times for an exemplary

TABLE 1

Table 1: Guidance on selection of initial inhalation volumes (as well as the numbers of breaths and estimated treatment times for an exemplary budesonide drug product and three different target delivered dose values)

| Height (cm) | Inhalation volume (L) | Inhalation time (s) at flow rate 6 L/min | Number of breaths per treatment: Low dose | Mid dose | High dose | Estimated treatment time (min): Low dose | Mid dose | High dose |
|---|---|---|---|---|---|---|---|---|
| ≤69 | 0.20 | 2 | 12 | 24 | 48 | 0.8 | 1.6 | 3.2 |
| 70-86 | 0.30 | 3 | 8 | 16 | 32 | 0.8 | 1.6 | 3.2 |
| 85-99 | 0.40 | 4 | 6 | 12 | 24 | 0.8 | 1.6 | 3.2 |
| 100-114 | 0.50 | 5 | 5 | 10 | 20 | 0.8 | 1.6 | 3.2 |
| 115-129 | 0.60 | 6 | 4 | 8 | 16 | 0.8 | 1.6 | 3.2 |
| 130-144 | 0.70 | 7 | 4 | 7 | 14 | 0.8 | 1.6 | 3.2 |
| >145 | 0.80 | 8 | 3 | 6 | 12 | 0.8 | 1.6 | 3.2 |

In one embodiment, the gas phase comprising the aerosol is administered during the inhalation period of the subject at a flow rate in the range of from about 4.8 L/min to 8.0 L/min; or from about 5.0 L/min to about 8.0 L/min; or from about 5.5 L/min to about 7.5 L/min; or from about 6.0 L/min to about 7.0 L/min; or from about 4.8 L/min to 7.2 L/min (such as 6.0 L/min); and at a total volume of the gas phase in the range of from about 0.20 L to about 0.80 L; or from about 0.30 L to about 0.80 L; or from about 0.40 L to about 0.80 L; or from about 0.60 L to about 0.80 L; for instance, at a flow rate of about 6 L/min; and at a total volume of the gas phase of about 0.20 L, or about 0.30 L, or about 0.40 L, or about 0.50 L, or about 0.60 L, or about 0.70 L, or about 0.80 L (each of these total volumes administered per inhalation phase). In one specific embodiment, the gas phase comprising the aerosol is administered during the inhalation period of the subject at a flow rate of 6.0 L/in; and at a total volume of the gas phase in the range of from about 0.40 L to about 0.80 L per inhalation; for instance, at a flow rate of 6.0 L/min and a total volume of 0.50 L, or at a flow rate of 6.0 L/min and a total volume of 0.60 L, or at a flow rate of 6.0 L/min and a total volume of 0.70 L.

It should be understood that by providing controlled inhalation flow rates and volumes as described above with the help of an inhalation device, the subject (i.e. the neonate, infant or child) is given a kind of artificial respiration since the inhalation device sets and adjusts the respiratory flow; however, unlike artificial respiration in the strict sense, the subject may still inhale and/or exhale spontaneously, too. In other words, the inhalation device provides a guidance how to inhale in the best manner to achieve deep lung deposition, and typically, the subjects follow these guided flow rates and volumes intuitively.

In one embodiment, the flow rate of the gas phase comprising the aerosol administered during the inhalation period of the subject is constant. It should be understood that the term 'constant' in that regard is still subject to minor fluctuations in most cases due to, for instance, the technical limitations of the compressor providing the flow of gas phase. Hence, a constant flow rate of x L/min means that the flow rate of the gas phase does not deviate more than ±30% from x, preferably not more than ±20%, and more preferably not more than 10%; e.g. 6 L/min±10%.

In one embodiment, the gas phase comprising the aerosol is administered via an inhalation interface comprising a mouthpiece or a facemask. In a specific embodiment, the gas phase comprising the aerosol is administered via an inhalation interface comprising a mouthpiece. In another specific embodiment, the gas phase comprising the aerosol is administered via an inhalation interface comprising a facemask.

It was found by the inventors that when using the parameters described above for the first aspect of the invention to administer the gas phase comprising the aerosol with a mouthpiece, the mouthpiece is much better accepted than normal, unregulated tidal breathing through a mouthpiece or a facemask. By adapting and controlling the flow rate of the administered gas phase, children are able to successfully perform inhalation treatments with a mouthpiece, unlike with conventional devices which do not provide such flow rate- and/or volume control. In addition, children were found to advantageously inhale deeper when guided to a pre-set inhalation volume.

In one embodiment, the gas phase comprising the aerosol is administered via an inhalation interface exhibiting a static dead volume ($DV_s$) between a nascent aerosol outlet at the upstream end of the inhalation interface and an outlet opening at the downstream end of the inhalation interface facing the subject's mouth of not more than 150 mL; or not more than 140 mL; or not more than 130 mL; or not more than 120 mL; or not more than 110 mL; or not more than 100 mL; or not more than 90 mL; or not more than 80 mL; or not more than 70 mL; or not more than 60 mL; or not more than 50 mL; or not more than 40 mL; or not more than 30 mL; or not more than 20 mL; or not more than 10 mL; for instance in the range of from about 1 mL to about 150 mL; or from about 1 mL to about 140 mL; or from about 1 mL to about 130 mL; or from about 1 mL to about 120 mL; or from about 1 mL to about 110 mL; or from about 1 mL to about 100 mL; or from about 1 mL to about 90 mL; or from about 1 mL to about 80 mL; or from about 1 mL to about 70 mL; or from about 1 mL to about 60 mL; or from about 1 mL to about 50 mL; or from about 1 mL to about 40 mL; or from about 1 mL to about 30 mL; or from about 1 mL to about 20 mL; or from about 1 mL to about 10 mL. In one of the preferred embodiments, the static dead volume ($DV_s$) between a nascent aerosol outlet at the upstream end of the inhalation interface and an outlet opening at the downstream end of the inhalation interface facing the subject's mouth is in the range of from about 1 mL to about 10 mL when working with a mouthpiece as the inhalation interface, and from about 1 mL to about 60 mL when working with a facemask as the inhalation interface.

Small static dead volumes, such as those described above, are of particular importance with neonates, infants and young children, because naturally the volumes they can inhale are already smaller than for adults, which inevitably results in the fact that less aerosol volume can be administered per inhalation. Therefore, it is preferred to not further decrease the aerosol volume which is administrable per inhalation. The static dead volumes of mouthpieces are typically smaller than with facemasks. Hence, in one of the preferred embodiments, the inhalation interface exhibiting the above-mentioned static dead volumes ($DV_s$) between the nascent aerosol outlet at the upstream end of the inhalation interface and the outlet opening at the downstream end of the inhalation interface facing the subject's mouth comprises a mouthpiece.

Herein resides one of the main advantages of the present invention. The inventors have surprisingly found that when controlling the inhalation flow rate and volumes as described above for the first aspect of the invention (in particular, when using a flow rate of e.g. 6 L/min and inhalation volumes of about 0.20 L, or about 0.30 L or about 0.40 L, particularly about 0.40 L), even neonates, infants and very young children of e.g. new-borns to about 2 years, or about 1 to 3 years, or 1 to 4 years, of age accepted the use of a mouthpiece and successfully inhaled the nebulised pharmaceutical composition through it. In fact, many of them tolerated the mouthpiece even better than the facemask which is believed to be partially due to the neonate's or infants' so-called 'oral stage'; i.e. to put something in its mouth on which to bite may be more pleasant to the neonate, infant or child than having a mask held against its face and covering most of it. The positive findings for mouthpieces was surprising because, prior to the present invention, this has not been considered feasible or advisable in prior art; the consensus being that neonates, infants and very young children of e.g. new-borns to about 2 years, or about 1 to 3 years, or 1 to 4 years, of age would object to mouthpieces and/or not be able to hold them in the mouth air-tightly.

In some cases, it may further be preferable that the nebulised drug is 'forced' into the peripheral lungs during inspiration with a mild overpressure such as to reduce the risk of drug being exhaled again during expiration and/or to reduce the amount exhaled. Hence, in one embodiment, the gas phase comprising the aerosol is administered at an overpressure of up to about 10 mbar; or up to about 5 mbar; or at an overpressure ranging from about 0.1 mbar to about 6 mbar; or from about 0.1 mbar to about 2 mbar; or from about 0.5 mbar to about 3 mbar; or from about 2 mbar to about 5 mbar. In one embodiment, the gas phase comprising the aerosol is administered at an overpressure of about 2 mbar. For instance, in one embodiment, as described above, the inhalation interface may comprise a facemask comprising a valve which opens from a closed to an open position in response to a pressure increasing from about 0.1 mbar to about 6 mbar; or from about 0.1 mbar to about 2 mbar; or from 0.5 mbar to 3 mbar; or from about 2 mbar to about 5 mbar; for instance, at an overpressure of about 2 mbar. When working with a mouthpiece on the other hand, typically no dedicated valves are required because the 'air-seal' formed by the lips around said mouthpiece gradually loosens naturally and breaks at about 10 mbar in most subjects, such that typically no higher overpressure is reached.

When the neonate, infant or child receives, or inhales, an actively provided, controlled flow of gas phase, this mild overpressure results naturally and inherently, unless the neonate, infant or child receives tries to actively inhale faster than the flow rate of from about 4 L/min to about 9 L/min provided, or from about 4.8 L/min to about 7.2 L/min, or from about 5.5 L/min to about 7.5 L/min, by the inhalation device; for instance, when the neonate, infant or child receives tries to actively inhale faster than 6 L/min. In this case, the mild overpressure would not build up, or only to a smaller extent. The inventors have found, though, that the majority of neonates, infants and children of not more than 12 years—such as from 1 to 8 years of age—readily accept the provided flow rate and inhalation volume provided, or emitted, by the inhalation device and adapt their breathing pattern to it very quickly and intuitively, or in other words 'follow' the flow of gas phase provided.

In a further embodiment the invention provides an inhalation device adapted to emit an inhalable pharmaceutical composition in the form of an aerosol comprised in a gas phase, the inhalation device comprising:

i. a facemask comprising an inhalation valve and an exhalation valve being configured to support an inhalation and/or exhalation with positive pressure support with a pressure ranging from about 0.1 mbar to about 6 mbar., ii. a jet nebuliser associated with the inhalation interface for generating the aerosol, iii. an electronically controlled compressor for providing a flow of gas phase to said jet nebuliser, iv. an electronic controller, wherein the electronic controller is adapted to directly control the operation of the electronically controlled compressor, and wherein the inhalation device is adapted to provide the complete gas phase comprising the aerosol through the nozzle of the jet nebuliser.

In a specific embodiment, the aerosol is administered via an inhalation interface comprising a facemask, wherein the facemask comprises an inhalation valve and an exhalation valve; optionally, inhalation- and exhalation valves being configured to open at 5 mbar (±3 mbar), or at 3 mbar (±2 mbar), when the inhalation or exhalation flow rate through the respective valve is 6 L/min in order to support an inhalation and/or exhalation with positive pressure support with a pressure ranging from 0.1 to 2 mbar; or from 0.5 mbar to 3 mbar; or from 2 mbar to 5 mbar. The facemask may comprise sealing means to seal the facemask to the face of the patient and to reduce losses of aerosol by use of a soft cushion or an elastic sealing lip adjusting the shape of the facemask sealing to the shape of the patient's face as well as to reduce deposition of aerosol in the eyes of the patient and allows to use the facemask with a breath-actuated inhalation device. Inhalation and exhalation valves may open at a pressure from 1 to 10 mbar, preferably 2 to 8 mbar to allow guidance of inhalation at a constant inhalation flow rate of in the range of from about 4 to about 9 L/min, or from about 4.8 L/min to about 7.2 L/min, or from about 5.5 to about 7.5 L/min. When the patient is inhaling with a positive pressure being guided by the constant inhalation flow rate from a console, the inhalation valve is normally closed and would only open when the patient would require additional air or the patient would not be capable of adapting to the constant inhalation flow rate provided for guiding inhalation.

In a specific embodiment, the inhalation interface comprises a facemask comprising an inhalation valve and an exhalation valve being configured to support an inhalation and/or exhalation with positive pressure support with a pressure ranging from about 0.1 mbar to about 6 mbar; or from about 0.1 mbar to about 2 mbar; or from about 0.5 mbar to about 3 mbar; or from about 2 mbar to about 5 mbar; for instance, at an overpressure of about 2 mbar.

Figure 2:
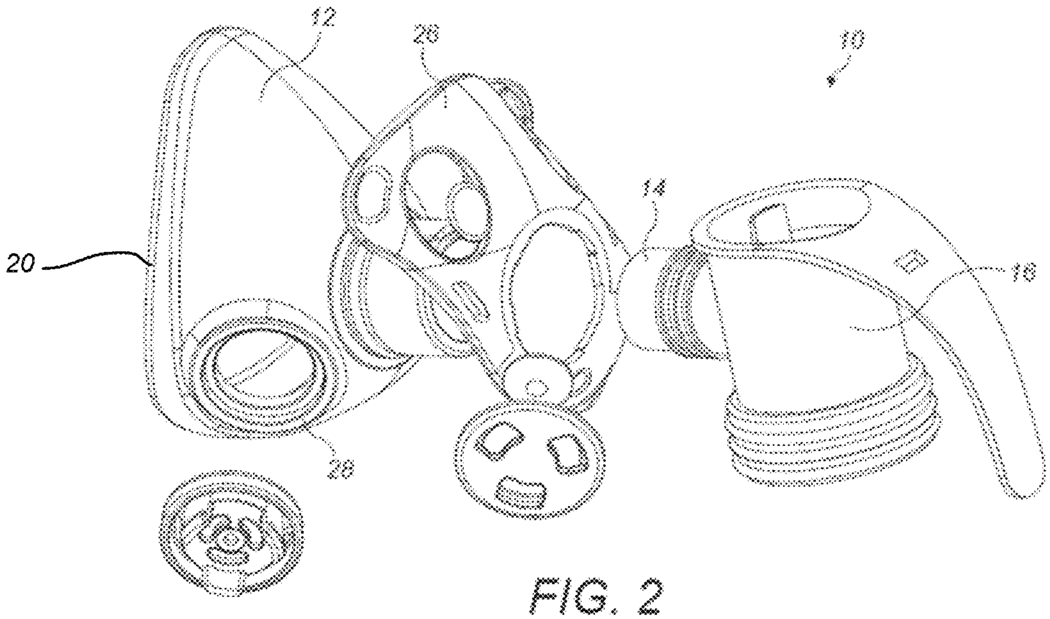
FIG. 2 shows an exploded view of the facemask depicted in FIG. 1.

An exemplary facemask is depicted in FIGS. 1 and 2. The facemask (10) comprises a mask body (12) and a connection port (14) for fluid connection with a nebuliser (not shown) using a conventional nebuliser handset (16). The depicted mask body (12) is configured to cover the mouth and nose of a patient; i.e. it is not a full-facemask which covers the eyes too. The mask body (12) is a generally semi-conical shaped shell, designed to be placed against the face of a patient. The shell defines a chamber (18) into which aerosolised medicament is received from a nebuliser via the connection port (14) and from which the patient inhales the aerosolised medicament. The shape of the shell may be optimised to fit either neonates, or infants or children aged 1 year to 10 years old; and is preferably translucent.

A cushion (20) extends around a peripheral extent of a patient side of the mask for improved patient comfort. The cushion also enables the facemask 10) to comfortably accommodate a range of patient head sizes. The cushion (20) is constructed from a first, soft, elastomeric material whereas the mask body (12) is made from a second material that is more rigid than the cushion (20). The cushion (20) may be co-moulded with the mask body (12). The mask body (12) is typically held in place against the patient's face using one or more straps or alternatively is simply held in place by the patient or caregiver by means of the rigid connection port and the nebuliser handset (16). The cushion (20) provides a sealing ring over the patient's mouth and nose.

The connection port (14) is tubular and open ended at both first and second ends (22, 24). At a first end (22), the connection port (14) extends outwardly from the mask body (12); i.e. in a direction away from the chamber (18). At the second, opposing end (24), the connection port (14) is configured to receive the nebuliser handset (16) in a conventional manner. The connection port (14) is preferably located centrally on a lower half of the mask body (12). This position is optimal because it is approximately in alignment with the location of a patient's mouth in use. This position minimises the loss of aerosolised medicament into 'dead space' within the mask body (12).

Optionally, a decorative motif (26), such as a teddy bear or other aesthetic designs, may be detachably attached to the mask body (12) about the central connection port (14). The purpose of the decorative motif (26) is primarily to make the facemask (10) more attractive and appealing to children. However, it also serves to improve the stability of the mask body (12).

As exemplified in FIG. 2, a first valve aperture (28) and a second valve aperture (not visible in FIG. 2) are located in the mask body (12). First (28) and second (not visible in FIG. 2) valve apertures are positioned either side of the connection port (14), approximately in vertical alignment therewith. Each valve aperture is a through-hole connecting the chamber (18) with the external surrounds and receives a respective a first/second valve. The valves are preferably tamper-proof.

Furthermore, the valves preferably have an opening pressure of 5 mbar (±3 mbar), or at 3 mbar (±2 mbar), at a flow rate of 6 L/min. This flow rate is suitable for neonates, infants and children younger than 12 years, or younger than 8 years, who naturally have a smaller lung capacity than adults. Conventional facemask valves typically only require very low pressure differences in order to open. An advantage of having an exhalation valve with such an opening pressure is that it allows the nebuliser to work with a slight overpressure. An advantage of having an inhalation valve is that it prevents asphyxia.

Alternatively, the facemask may incorporate a single bi-directional valve, optionally a hysteresis type valve, with an opening pressure for inhalation that is higher than the opening pressure for exhalation. This ensures that a positive pressure is maintained within the chamber of the mask body (12). Also, a lower pressure is required to maintain the valve open, once opened. This arrangement is more comfortable for the patient during exhalation.

In one embodiment, the inhalable pharmaceutical composition is administered as described above using an inhalation device which comprises an aerosol generator. In a further embodiment, this aerosol generator is inhalation-triggered (also called breath-actuated). In a specific embodiment, the aerosol generator comprises a nebuliser; or a metered dose inhaler (MDI); or a dry powder inhaler (DPI). In a more specific embodiment, the aerosol generator comprises a nebuliser selected from jet nebulisers or vibrating mesh nebulisers. In a yet more specific embodiment, the aerosol generator comprises a jet nebuliser operating at a nominal nebulising pressure in the range of 1.6 bar to 2.0 bar; e.g. at a nominal nebulising pressure of 1.8 bar; optionally, this pressure results in a flow rate of the gas phase comprising the aerosol of about 6 L/min.

In one embodiment according to the first aspect of the invention, the inhalable pharmaceutical composition is provided for use in the therapy of a subject suffering from a disease selected from the group consisting of pulmonary diseases, diabetes and allergies; for use in vaccination; and/or for use in immunotherapy. In one embodiment according to the first aspect of the invention, the inhalable pharmaceutical composition is provided for use in the therapy, or is administered in the therapy, of a subject suffering from a disease, optionally a pulmonary disease. In a specific embodiment, the disease is a pulmonary disease selected from the group of bronchitis, asthma, chronic obstructive pulmonary disease (COPD), pneumonia, cystic fibrosis (CF), idiopathic pulmonary fibrosis (IPF), pulmonary arterial hypertension (PAH), pulmonary alveolar proteinosis (PAP), respiratory distress syndrome (RDS), acute bronchitis, bronchitis, bronchiectasis, primary ciliary dyskinesia, respiratory syncytial virus infection (RSV), chronic cough, or lung cancer. In a specific embodiment, the pulmonary disease is asthma. In a further specific embodiment, the inhalable pharmaceutical composition is administered in the maintenance therapy of a subject suffering from mild, intermittent asthma; asthma controlled with inhaled corticosteroids (ICS); asthma controlled with ICS and add on therapy (e.g. ICS and short-acting beta$_2$-agonists SABA); persistent, poorly controlled asthma; or persistent, poorly controlled asthma with frequent use of oral steroids. In one embodiment, the composition is provided for use in the therapy of mild to moderate persistent asthma.

In one embodiment according to the first aspect of the invention, the inhalable pharmaceutical composition is a steroid composition. In a specific embodiment, the inhalable pharmaceutical composition is a corticosteroid composition. In a more specific embodiment, the inhalable pharmaceutical composition is a glucocorticoid composition. In a yet more specific embodiment, the inhalable pharmaceutical composition comprises a glucocorticoid selected from budesonide, fluticasone propionate, beclomethasone dipropionate, ciclesonide, flunisolide, mometasone furoate, and triamcinolone acetonide. In a specific embodiment, the inhalable pharmaceutical composition comprises budesonide.

In one embodiment, the inhalable steroid composition is provided in form of a suspension; for instance, an inhalable budesonide suspension. When administering suspensions, such as budesonide suspensions, the droplet size is typically raised by about 1 μm compared to inhalation solutions. Here, the administration according to the first aspect of the invention is particularly useful, because this increase in droplet size causes most of the inhaled aerosol to be deposited in the throat of the child, and this detrimental throat deposition can be limited by reducing the inhalation flow rate to about 4 L/min to about 9 L/min, or from about 4.8 L/min to about 7.2 L/min, or from about 5.5 L/min to about 7.5 L/min (e.g. 6 L/min).

In one embodiment, the inhalable steroid composition is provided in form of an inhalable budesonide suspension with a concentration of at least 0.4 mg/mL budesonide; for instance, in the range of 0.4 mg/mL to 1.0 mg/mL, or 0.4 mg/mL to 0.8 mg/mL, or 0.4 mg/mL to 0.6 mg/mL, e.g. 0.5 mg/mL. In a specific embodiment, the inhalable steroid composition is provided in form of an inhalable budesonide suspension with a concentration of at least 0.4 mg/mL budesonide (e.g. 0.5 mg/mL), wherein said composition is administered as an aerosol, and wherein said aerosol is comprised in a gas phase, and wherein said gas phase is generated by an inhalation device which is adapted to nebulise a filling volume of not more than 1.4 mL, or not more than 1.3 mL, or not more than 1.2 mL.

In a specific embodiment, the invention according the first aspect of the invention provides an inhalable budesonide suspension for use in the therapy of a subject suffering from asthma, the subject being a neonate, an infant or a child younger than 12 years, or from 1 to 8 years, wherein said composition is administered as an aerosol, and wherein said aerosol is comprised in a gas phase, and wherein said gas phase is generated by an inhalation device which is adapted to emit said gas phase and administer it to said subject (a) at a constant flow rate of about 6 L/min during the inhalation period of the subject, and (b) at a total volume of about 0.20 L or 0.40 L or 0.6 L or 0.8 L per inhalation via an inhalation interface comprising a mouthpiece and exhibiting a static dead volume ($DV_s$) between a nascent aerosol outlet at the upstream end of the inhalation interface and an outlet opening at the downstream end of the inhalation interface facing the subject's mouth of not more than 50 mL (e.g. from 1 mL to 10 mL), optionally at an overpressure of up to about 10 mbar (e.g. from 0.5 mbar to 3 mbar, such as at 2 mbar).

In a further specific embodiment, the invention according the first aspect of the invention provides an inhalable budesonide suspension for use in the therapy of a subject suffering from asthma, the subject being a neonate, an infant or a child younger than 12 years, or from 1 to 8 years, wherein said composition is administered as an aerosol, and wherein said aerosol is comprised in a gas phase, and wherein said gas phase is generated by an inhalation device which is adapted to emit a target delivered dose ranging from 10 μg to 70 μg, with a low-dose ranging from 10 μg to 25 μg, preferably 15 μg to 20 μg; or mid-dose ranging from 25 μg to 45 μg, preferably 30 μg to 40 μg; and a high-dose ranging from 45 μg to 75 μg, preferably 60 μg to 70 μg at the mouthpiece or face-mask of the inhalation device, whereas the different target dosages are adjusted individually to the patient to control asthma symptoms.

In one embodiment, the inhalation device according to the present invention is adapted for the treatment of asthma in children to emit an inhalable pharmaceutical budesonide composition, and further adapted to deliver a dose of 15 μg, 30 μg or 60 μg at the mouthpiece or facemask of the inhalation device.

The target delivered dose may be pre-set by the cumulative nebulization time for one treatment session. For one selected dose, the number of breaths required to complete one treatment session is dependent on the nebulisation time per breath. In one embodiment the cumulative nebulisation times for one treatment session are 24 seconds for the 15 μg, 48 seconds for 30 μg and 96 seconds for 60 μg budesonide (also see e.g. Table 1 above), whereas the cumulative nebulisation time is achieved by inhalation of several breaths with a pre-set nebulisation time per breath with possible nebulisation and inhalation times of 2, 3, 4, 5, 6, 7 or 8 seconds, which is selected by the patient, caregiver or healthcare professional before start of the treatment session or which is adjusted during the treatment session to ensure that the patient is performing a deep and comfortable inhalation. The delivered dose rate is ranging from 0.4 to 1.5 μg per second preferably 0.5 to 0.8 μg per second. In case of a higher performing nebuliser, cumulative nebulisation times per treatment session may be reduced. Initially, inhalation times for one treatment session were estimated by calculation but first clinical trials in patients have shown that these estimated inhalation times match well with the treatment times achieved by subjects.

In an alternative embodiment, the invention according the first aspect of the invention provides an inhalable budesonide suspension for use in the therapy of a subject suffering from asthma, the subject being a neonate, an infant or child younger than 12 years, or from 1 to 8 years, wherein said composition is administered as an aerosol, and wherein said aerosol is comprised in a gas phase, and wherein said gas phase is generated by an inhalation device which is adapted to emit said gas phase and administer it to said subject (a) at a constant flow rate of about 6 L/min during the inhalation period of the subject, and (b) at a total volume of about 0.20 L or 0.40 L or 0.6 L or 0.8 L per inhalation via an inhalation interface comprising a facemask and exhibiting a static dead volume ($DV_s$) between a nascent aerosol outlet at the upstream end of the inhalation interface and an outlet opening at the downstream end of the inhalation interface facing the subject's mouth of not more than 150 mL (e.g. from 1 mL to 60 mL), optionally at an overpressure of up to about 5 mbar; e.g. from 0.5 mbar to 3 mbar such as 2 mbar.

In a second aspect, the invention provides an inhalation device adapted to emit an inhalable pharmaceutical composition in the form of an aerosol comprised in a gas phase, the inhalation device comprising:

(i) an inhalation interface for providing the emitted aerosol in the gas phase to the airways of a subject, (ii) a jet nebuliser associated with the inhalation interface for generating the aerosol, (iii) an electronically controlled compressor for providing a flow of gas phase to said jet nebuliser, (iv) an electronic controller, wherein the electronic controller is adapted to directly control the operation of the electronically controlled compressor, and wherein the inhalation device is adapted to provide the complete gas phase comprising the aerosol through the nozzle of the jet nebuliser at a controlled flow rate.

Figure 3A:
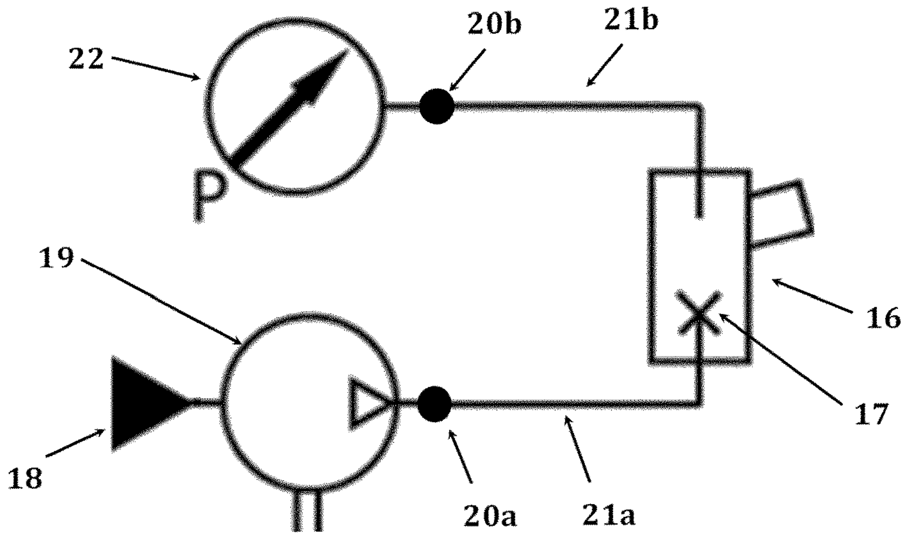
FIGS. 3A and 3B show exemplary inhalation devices according to the second aspect of the invention.
Figure 3B:
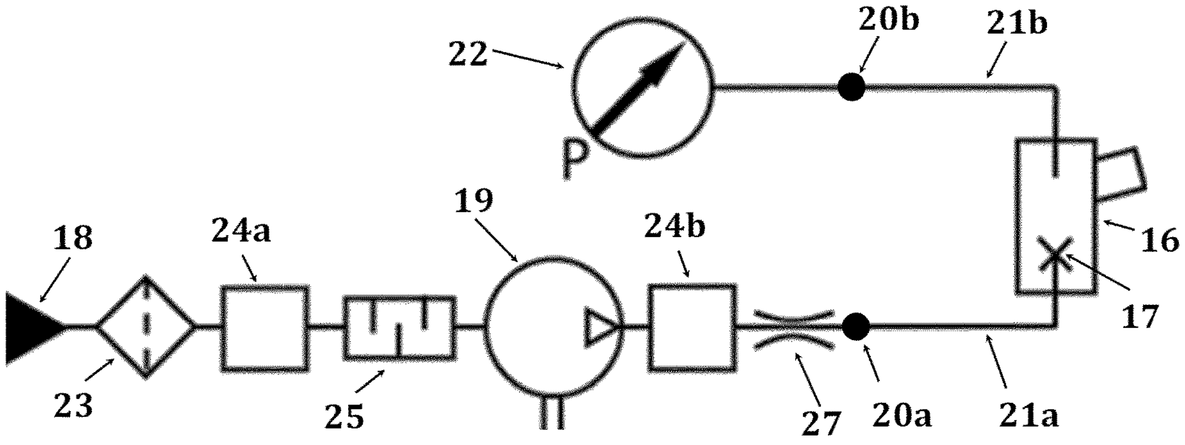

Exemplary inhalation devices according to the second aspect of the invention are depicted in FIGS. 3A and 3B. FIG. 3A is showing the most simple set-up comprising an air inlet (18) to allow air to enter the electronically controlled compressor (19; the electronic controller as such is not depicted), flexible tubing (21*a*; the 'nebuliser tube') attached via connector (20*a*) and leading from said compressor (19) to the jet nebuliser (17) which is housed at the bottom, or lower end, of an inhalation interface in the form of a light-weight, hand-held handset (16). At the top, or upper end, of said handset (16), a further flexible tubing (21*b*; the 'manometer tube') is attached via connector (20*b*), said tubing leading to a pressure gauge, or manometer (22). However, there is no air-flow provided from the pressure gauge, or manometer (22) to the jet nebuliser (17) via said 'manometer tube' (21*b*). Instead, the complete gas phase which is to be inhaled and which comprises the aerosol is provided by the electronically controlled compressor (19) and through the nozzle of the jet nebuliser (17). In other words, there is no separate 'support-air flow' or 'additional air flow' that is intentionally mixed with said complete gas phase coming from the nozzle of the jet nebuliser (17) in order to form a cumulative gas phase and thereby deliver the aerosol with a cumulative gas phase. For instance, there is no separate 'support-air flow' provided passively via valves in the inhalation interface (e.g. any of the valves in the handset (16) and/or the attached mouthpiece or facemask). Furthermore, there is also no separate 'support-air flow' provided actively by a separate compressor to a position of the handset (16) other than the nozzle of the jet nebuliser (17), such as to the top of the handset (16).

For the avoidance of misunderstandings, this does not mean that there cannot be a second or further electronically controlled compressor (19) in the device according to the second aspect of the invention; however, if indeed a second or further compressor (19) is provided, the inhalation device is still adapted to provide the complete gas phase of both, or all, these compressors through the nozzle of the jet nebuliser. Similarly, the above also does not mean that a user of the inhalation device (e.g. a neonate, infant or child) would never inhale, or be able to inhale, any air volume in addition to the complete gas phase coming from the nozzle of the jet nebuliser (17); for instance, if the face mask were not pressed tightly enough onto the user's face during inhalations, or if the user were to inhale very forcefully and thereby managed to unintentionally suck in air via any of the valves potentially provided in the inhalation interface, there could be very small volumes of additional air which were not provided by the electronically controlled compressor (19) and through the nozzle of the jet nebuliser (17). However, these small volumes are not intended and not needed for successful delivery of inhalation compositions.

In this aspect, the device according to the second aspect of the invention clearly differs from prior art devices, such as the older versions of the inventors' devices known as AKITA®. In said older devices, the gas phase comprising the aerosol was never passed completely through the nozzle of the jet nebuliser at a controlled flow rate. Instead, with the older devices the gas phase comprising the aerosol was the result of at least two cumulative air flows, or air streams:

one, the 'nebulising air flow', provided to and through the nozzle of the jet nebuliser at sufficiently high pressure to disperse the liquid drug formulations into inhalable droplets and thus form a dense nascent aerosol, and a separate one, the 'support air-flow'—typically at a far lower pressure than required at the jet nebuliser nozzle—provided at a controlled flow rate to a position of the inhalation interface other than the nozzle of the jet nebuliser so as to mix the dense nascent aerosol with the 'support air-flow' prior to inhalation; for instance, to the top of a handset, with the jet nebuliser sitting at the bottom of said handset. These at least two cumulative air flows were either provided by two or more pressurised air sources; or by one pressurised air source initially generating a single air flow that was subsequently split up into the 'nebulising air flow' through the jet nebuliser nozzle and the 'support air flow'.

The expression 'directly controlled'—as in 'wherein the electronic controller is adapted to directly control the operation of the electronically controlled compressor' (19)—is to be understood such that the electronic controller is controlling the operation of the compressor directly rather than, for instance, said electronic controller controlling a valve, or a set of valves, separate from said compressor, with said valve(s) then 'releasing' the pressurised air provided by the compressor in a controlled manner to the inhalation interface, and if necessary distributing said pressurised air between the 'nebulising air flow' and the 'support air flow' paths. In that regard, the electronically controlled compressor (19) and the electronic controller operate similar to an air pump, or tyre inflator, controlled by a user's hand movement: when the user pushes the piston down and towards the pump's nozzle (i.e. when the controller switches the compressor on), a defined volume of air is expelled through the nozzle and into the tyre, with the hand's movement defining the flow rate; once the hand and piston rest (i.e. if the controller switches the compressor off), no further air is expelled. In one embodiment of such 'direct control' of the electronically controlled compressor (19), the electronic controller can, for instance, switch it on during inhalations, and switch it off during exhalations if the device is breath-actuated; thereby either delivering gas phase to and through the jet nebuliser nozzle or not for the inhalation or exhalation, respectively. Alternatively, or in addition hereto, the electronic controller can switch the compressor on and off for pre-programmed sets of time.

In this aspect, the device according to the second aspect of the invention differs from prior art devices such as the one described in U.S. Pat. No. 6,606,989 B1. In this earlier disclosure of the inventors, the compressor is providing pressurised air into a reservoir from which the pressurised air is 'released' by computer-controlled, breath-actuated valves. In other words, the electronic controller is controlling the valves, not the compressor in order to provide the desire flow rate and volume at the inhalation interface.

While the inhalation device according to the second aspect of the invention can also be used for inhalation therapies of adults, it is particularly suited for inhalation therapies of neonates, infants or children younger than 12 years, or from 1 to 8 years, in that it allows for particularly low, yet stable flow rates.

In one embodiment, the inhalation device according to the second aspect of the invention is adapted to provide the complete gas phase comprising the aerosol through the nozzle of the jet nebuliser at a flow rate of from about 4 L/min to about 9 L/min, or from about 4.8 L/min to about 7.2 L/min, or from about 5.5 L/min to about 7.5 L/min, such as 6 L/min. In a specific embodiment, it is the electronically controlled compressor that provides the complete gas phase comprising the aerosol through the nozzle of the jet nebuliser at a controlled flow rate; for instance, at a flow rate of from about 4 L/min to about 9 L/min, or from about 4.8 L/min to about 7.2 L/min, or from about 5.5 L/min to about 7.5 L/min, such as 6 L/min. As will be detailed further below this may, for instance, be achieved with an electronically controlled compressor exhibiting a nominal operating pressure of at least 1.2 bar; or at least 1.3 bar; or at least 1.4 bar; or at least 1.5 bar; or at least 1.6 bar; or at least 1.7 bar; or at least 1.8 bar; for instance, a nominal operating pressure in the range of 1.6 bar to 2.0 bar, such as a nominal operating pressure of 1.8 bar.

In one of the preferred embodiments, the operation of the electronically controlled compressor is breath-actuated, or inhalation-triggered, i.e. it commences its operation—and hence, provides gas phase to the jet nebuliser—only when sensing an inhalation. In a specific embodiment, the operation of the electronically controlled compressor is breath-actuated, or inhalation-triggered, by means of a pressure sensor responsive to a suction pressure in, or at, the inhalation interface.

In one embodiment, the inhalation device is adapted to emit the aerosol in the gas phase during the inhalation period of the subject. In a specific embodiment, the inhalation device is adapted to emit the aerosol in the gas phase during the complete inhalation period of the subject. Alternatively, or in addition thereto, the electronic controller may be adapted to directly control the operation of the electronically controlled compressor in such a way as to stop the operation of the compressor after a pre-set time; for instance, after 1 second; or after 2 seconds; or after 3 seconds; or after 4 seconds; or after 5 seconds, or after 6 seconds; or after 7 seconds; or after 8 seconds. In other words, with the electronically controlled compressor being directly controlled by the electronic controller (e.g. in response to an inhalation trigger), not only the onset of the compressor's operation but also the duration thereof can be controlled. This time, or duration, may be pre-set at the inhalation device of the invention, e.g. by a doctor or by a caregiver. This embodiment is preferred, because the longer the pre-set 'inhalation time' is selected, the deeper the inhalation and the higher the pre-set inhalation volume resulting from said time; i.e. the more aerosol may be delivered per inhalation.

As mentioned above, it is theoretically possible to adapt the device to also emit the gas phase comprising the aerosol during the exhalation period; however, this is usually not advisable, due to the unfavourable losses of the inhalable pharmaceutical composition as well as the potential contamination of the ambient air in the room where the composition is administered. Therefore, in one of the preferred embodiments of the invention's second aspect, the inhalation device is adapted to emit the aerosol in the gas phase at a flow rate of from about 4 L/min to about 9 L/min, or from about 4.8 L/min to about 7.2 L/min, or from about 5.5 L/min to about 7.5 L/min (e.g. 6 L/min) only during the inhalation period of the neonate, infant or child, whereas no gas phase, and in particular no gas phase comprising aerosol, is emitted during the exhalation phase. Alternatively, the gas phase comprising the aerosol may be emitted at a flow rate of from about 4 L/min to about 9 L/min, or from about 4.8 L/min to about 7.2 L/min, or from about 5.5 L/min to about 7.5 L/min (e.g. 6 L/min) during the inhalation period of the neonate, infant or child, whereas a far lower flowrate of below 2 L/min, preferably below 1 L/min is used during the exhalation phase; e.g. about 0.8 L/min or about 0.5 L/min.

In one embodiment, the flow rate of the gas phase comprising the aerosol emitted during the inhalation period of the subject is constant. In other words, the electronically controlled compressor of the inhalation device provides, or emits, the gas phase comprising the aerosol at a constant flow rate; for instance, at a flow rate of from about 4 L/min to about 9 L/min, or from about 4.8 L/min to about 7.2 L/min, or from about 5.5 L/min to about 7.5 L/min, such as 6 L/min. As mentioned earlier, the term 'constant' should be understood to still allow for minor fluctuations due to, for instance, the technical limitations of the electronically controlled compressor providing the flow of gas phase. A constant flow rate of 'x L/min' as used herein shall thus mean that the flow rate of the gas phase does not deviate more than ±30% from x, preferably not more than ±20%, and more preferably not more than 10%; e.g. 6 L/min±10%.

This constant flow rate also results in the inhalation device of the invention being capable of controlling both the inhalation flow rate and the inhalation volume per inhalation if the inhalation time is pre-set as described above. Hence, in one embodiment, the inhalation time may be pre-set with the inhalation device; for instance, pre-set with the electronic controller of the inhalation device.

As mentioned above, it shall be understood that by providing controlled inhalation flow rates and controlled inhalation volumes with the inhalation device, the subject (i.e. the neonate, infant or child) is given a kind of artificial respiration; however, unlike artificial respiration in the strict sense, the subject may still inhale and/or exhale spontaneously, too. In other words, the inhalation device provides a guidance how to inhale in the best manner to achieve deep lung deposition, and typically, the subjects follow these guided flow rates and volumes intuitively.

In a further preferred embodiment, the inhalation device according to the second aspect comprises only one, or only a single, electronically controlled compressor. In a specific embodiment, said single electronically controlled compressor, whose operation is directly controlled by the electronic controller, is adapted to provide, or emit, a pre-set inhalation volume at a target flow rate; for instance, a volume of about 0.10 L to about 0.80 L per inhalation, at a flow rate of from about 4 L/min to about 9 L/min, or from about 4.8 L/min to about 7.2 L/min, or from about 5.5 L/min to about 7.5 L/min, such as 6 L/min.

In one embodiment, the inhalation device neither comprises nor requires any flow-control-valves, i.e. no valves for controlling the flow of the gas phase with regards to specific target flow rates and/or volumes (e.g. the about 4 L/min to about 9 L/min and/or the about 0.10 L to about 0.80 L per inhalation). In other words, the inhalation flow rate, the inhalation volume, or preferably both, may be controlled by controlling the compressor rather than e.g. by using dedicated flow-control valves, or regulating valves (such as those described in U.S. Pat. No. 6,606,989 B1). This is advantageous in that a) the device comprises fewer components, and b) in that—unlike in U.S. Pat. No. 6,606,989 B1—the electronically controlled compressor is not working constantly but only when actually required for providing a gas flow for nebulising and inhalation, which ultimately reduces the wear on the compressor and its energy consumption.

In one embodiment, the inhalation device does not require any additional support flow means, i.e. no additional means to create and/or amplify a support flow of gas phase in parallel to the 'main' gas phase which is provided, or emitted, through the nozzle of the jet nebuliser. For instance, in a specific embodiment, the inhalation device does not require any additional compressors (in addition to the electronically controlled compressor). In another specific embodiment, the inhalation device does not require any venturi-type flow amplifiers. In a more specific embodiment, the inhalation device neither comprises additional compressors nor any venturi-type flow amplifiers. In other words, the complete gas phase required for nebulising the inhalable pharmaceutical composition and for providing the desired target inhalation flow rate of, for instance, from about 4 L/min to about 9 L/min, or from about 4.8 L/min to about 7.2 L/min, or from about 5.5 L/min to about 7.5 L/min, is provided by the electronically controlled compressor—optionally a single one—through the nozzle of the jet nebuliser.

With only one electronically controlled compressor, no flow-control valves and/or no additional support flow means being required, the inhalation device according to the second aspect of the invention is advantageously simplified compared to prior art devices in terms of e.g. the components required and the mechanisms of operation.

In one embodiment, the inhalation interface of the inhalation device according to the second aspect of the invention comprises a mouthpiece or a facemask.

In one embodiment of the inhalation device according to the second aspect of the invention, the inhalation interface exhibits a static dead volume ($DV_s$) between a nascent aerosol outlet at the upstream end of the inhalation interface and an outlet opening at the downstream end of the inhalation interface facing the subject's mouth of not more than 150 mL; or not more than 140 mL; or not more than 130 mL; or not more than 120 mL; or not more than 110 mL; or not more than 100 mL; or not more than 90 mL; or not more than 80 mL; or not more than 70 mL; or not more than 60 mL; or not more than 50 mL; or not more than 40 mL; or not more than 30 mL; or not more than 20 mL; or not more than 10 mL; for instance in the range of from about 1 mL to about 150 mL; or from about 1 mL to about 140 mL; or from about 1 mL to about 130 mL; or from about 1 mL to about 120 mL; or from about 1 mL to about 110 mL; or from about 1 mL to about 100 mL; or from about 1 mL to about 90 mL; or from about 1 mL to about 80 mL; or from about 1 mL to about 70 mL; or from about 1 mL to about 60 mL; or from about 1 mL to about 50 mL; or from about 1 mL to about 40 mL; or from about 1 mL to about 30 mL; or from about 1 mL to about 20 mL; or from about 1 mL to about 10 mL. In one of the preferred embodiments, the static dead volume ($DV_s$) between a nascent aerosol outlet at the upstream end of the inhalation interface and an outlet opening at the downstream end of the inhalation interface facing the subject's mouth is in the range of from about 1 mL to about 10 mL when working with a mouthpiece as the inhalation interface, and from about 1 mL to about 60 mL when working with a facemask as the inhalation interface.

Since a jet nebuliser is associated with the inhalation interface of the inhalation device according to the second aspect of the invention, the nascent aerosol outlet at the upstream end of the inhalation interface is typically understood to be positioned at the nozzle of this jet nebuliser, i.e. at the point where the nascent aerosol is released into the inhalation interface.

In one of the preferred embodiments, the inhalation interface exhibits a static dead volume ($DV_s$) between a nascent aerosol outlet at the upstream end of the inhalation interface and an outlet opening at the downstream end of the inhalation interface facing the subject's mouth of not more than 50 mL; for instance, in the range of from about 5 mL to about 50 mL; or from about 2 mL to about 50 mL; or from about 1 mL to about 50 mL. In one of the further preferred embodiments, the inhalation interface exhibits a static dead volume ($DV_s$) between a nascent aerosol outlet at the upstream end of the inhalation interface and an outlet opening at the downstream end of the inhalation interface facing the subject's mouth of not more than 40 mL; for instance, in the range of from about 5 mL to about 40 mL; or from about 2 mL to about 40 mL; or from about 1 mL to about 40 mL. In one of the yet further preferred embodiment, the inhalation interface exhibits a static dead volume ($DV_s$) between a nascent aerosol outlet at the upstream end of the inhalation interface and an outlet opening at the downstream end of the inhalation interface facing the subject's mouth of not more than 30 mL; for instance, in the range of from about 5 mL to about 30 mL; or from about 2 mL to about 30 mL; or from about 1 mL to about 30 mL.

In particular, when working with a mouthpiece such small static dead volumes ($DV_s$) could be achieved. Therefore, in one of the preferred embodiments, the inhalation interface comprises a mouthpiece. In a specific embodiment, the inhalation interface comprises a mouthpiece and exhibits static dead volume ($DV_s$) between a nascent aerosol outlet at the upstream end of the inhalation interface and an outlet opening at the downstream end of the inhalation interface facing the subject's mouth of not more than 50 mL; or not more than 40 mL; or not more than 30 mL; or not more than 20 mL; or not more than 10 mL; for instance in the range of from about 1 mL to about 50 mL; or from about 1 mL to about 40 mL; or from about 1 mL to about 30 mL; or from about 1 mL to about 20 mL; or from about 1 mL to about 10 mL. In one of the preferred embodiments, when working with a mouthpiece, the static dead volume ($DV_s$) between a nascent aerosol outlet at the upstream end of the inhalation interface and an outlet opening at the downstream end of the inhalation interface facing the subject's mouth is in the range of from about 1 mL to about 10 mL.

In an alternative embodiment, the inhalation interface comprises a facemask. In a specific embodiment, the inhalation interface comprises a facemask and exhibits static dead volume ($DV_s$) between a nascent aerosol outlet at the upstream end of the inhalation interface and an outlet opening at the downstream end of the inhalation interface facing the subject's mouth of not more than 150 mL; or not more than 140 mL; or not more than 130 mL; or not more than 120 mL; or not more than 110 mL; or not more than 100 mL; or not more than 90 mL; or not more than 80 mL; or not more than 70 mL; or not more than 60 mL; for instance in the range of from about 1 mL to about 150 mL; or from about 1 mL to about 140 mL; or from about 1 mL to about 130 mL; or from about 1 mL to about 120 mL; or from about 1 mL to about 110 mL; or from about 1 mL to about 100 mL; or from about 1 mL to about 90 mL; or from about 1 mL to about 80 mL; or from about 1 mL to about 70 mL; or from about 1 mL to about 60 mL. In one of the preferred embodiments, when working with a facemask, the static dead volume ($DV_s$) between a nascent aerosol outlet at the upstream end of the inhalation interface and an outlet opening at the downstream end of the inhalation interface facing the subject's mouth is in the range of from about 1 mL to about 60 mL.

In a specific embodiment the inhalation interface comprises a facemask comprising an inhalation valve and an exhalation valve being configured to support an inhalation and/or exhalation with positive pressure support with a pressure ranging from about 0.1 mbar to about 6 mbar; or from about 0.1 mbar to about 2 mbar; or from about 0.5 mbar to about 3 mbar; or from about 2 mbar to about 5 mbar; for instance, at an overpressure of about 2 mbar.

As mentioned earlier, most prior art devices are often not 'tailored' towards neonates, infants or children, and not designed to perform well, for instance, at the flow rates and/or inhalation volumes that are used by neonates, infants or children. For instance, children inhale with very low inhalation volumes. Therefore, for them the static dead volume ($DV_s$) of the inhalation interface is particularly important since the ratio of $DV_s$ to total inhalation volume is larger than with adults (compare e.g. 145 mL $DV_s$ in 400 mL inhalation volume versus 145 mL $DV_s$ in 2000 mL inhalation volume). Devices which are not optimised in that regard often make deposition and/or dosing inefficient in neonates, infants and children younger than 12 years. A first step of tailoring the inhalation device towards neonates, infants or children is to prefer the use of a mouthpiece over using facemasks.

Alternatively, or in addition thereto, the dead volume may be reduced further. For instance, in one embodiment, the inhalation device according to the second aspect of the invention is adapted such as to prevent, or at least limit, exhalation into or through the inhalation device. In a specific embodiment, the inhalation interface is adapted such as to prevent, or at least limit, exhalation into or through the inhalation device; i.e. when attempting to exhale into or through the inhalation device, the neonate, infant or child would meet a resistance. Instead, the inhalation interface is briefly moved away from the face, or mouth, of the neonate, infant or child during exhalations. This provision offers the important benefit that no, or almost no, exhaled air is introduced into the inhalation device, or specifically inhalation interface; in other words, the gas phase comprising the aerosol, which was emitted to the neonate, infant or child via said inhalation interface during the preceding inhalation phase is not 'diluted' and/or 'blown away' or pushed out of the nebuliser by the exhalation flow or clean air. This means that the gas phase comprising the aerosol remains mostly stagnant within the inhalation interface and is 'stored' there until the next inhalation is actuated by the neonate, infant or child. In this way the virtual dead volume ($DV_v$) achieved after the first initial inhalation can be reduced even further; thereby, advantageously increasing the fraction of aerosol in the total inhalation volume.

Unlike the static dead volume ($DV_s$) which is defined by the actual physical dimensions of the inhalation interface between the nascent aerosol outlet at the upstream end of the inhalation interface and the outlet opening at the downstream end of the inhalation interface facing the subject's mouth, the term virtual dead volume ($DV_v$) shall refer to said fraction of the static dead volume ($DV_s$) which—during use of the inhalation device—does not remain filled with the aerosol-comprising gas phase; for instance, because the subject tries to exhale forcefully into the inhalation interface and/or because of partial losses of the aerosol-comprising gas phase during the exhalation phase when the inhalation interface is moved away from the subject's face or mouth.

In one embodiment, the inhalation interface comprises a mouthpiece and exhibits a virtual dead volume ($DV_v$) of not more than 15 mL; or not more than 10 mL; or not more than 5 mL; for instance, in the range of from about 1 mL to about 15 mL; or from about 1 mL to about 10 mL; or from about 1 mL to about 5 mL. In some cases, the virtual dead volume ($DV_v$) of the inhalation interface comprising a mouthpiece is even reduced to zero millilitres. This is mostly possible due to the narrower, cylindrical shape and the smaller opening of mouthpieces in comparison to facemasks.

With inhalation interfaces comprising facemasks, the virtual dead volume ($DV_v$) is typically larger, because of its larger opening; when it is removed from the face briefly for exhalation, the gas phase comprising the aerosol standing in the facemask after an inhalation is more easily 'diluted' with and/or 'blown away' by ambient air and thus increases the virtual dead volume ($DV_v$). In one embodiment, the inhalation interface comprises a facemask and exhibits a virtual dead volume ($DV_v$) of not more than 100 mL; or not more than 90 mL; or not more than 80 mL; or not more than 70 mL; or not more than 60 mL; or not more than 50 mL; or not more than 40 mL; or not more than 30 mL; or not more than 20 mL; or not more than 10 mL; or not more than 5 mL; for instance, in the range of from about 1 mL to about 60 mL; or from about 1 mL to about 50 mL; or from about 1 mL to about 40 mL.

The smaller virtual dead volumes ($DV_v$) of mouthpieces render them particularly suited for use in an inhalation device optimised for neonates, infants and children younger than 12 years (e.g. from 1 to 8 years; also called a paediatric inhalation device), and in particular suitable for neonates, infants and children not older than 4 years. However, as mentioned above, prior to the present invention, the broad agreement was that the use of mouthpieces with neonates, infants and very young children of e.g. about 1 to 3 years, or 1 to 4 years, of age was not even considered possible. However, the inventors surprisingly found that even neonates and infants as young as 0 to 3 years, or 1 year to 3 years, or 1 year to 2 years, or even 0 year to 2 years, are capable of inhaling a nebulised pharmaceutical composition successfully through a mouthpiece, especially when providing an inhalation flow with controlled flow rate and volume as described above.

In order to provide the above-mentioned controlled inhalation flow using a directly controlled, breath actuated compressor, the inhalation device according to the second aspect of the invention requires a compressor that is quick and powerful, such as to reach the desired target flow rate in as little time as possible and to allow fast onset of the required nebulising pressure at the nozzle. At the same time, the directly controlled, breath actuated compressor creates air flow oscillations to some degree, and the so-called conducting volume (e.g. the pump head space, the tubing towards the nebuliser nozzle, etc.) should preferably be configured in such a way as to provide a conducting volume that still achieves sufficient damping, or 'diluting', of said air flow oscillations while allowing for the fast pressure rise within not more than 500 ms, preferably less.

In one embodiment, the electronically controlled compressor is capable of establishing the flow rate within not more than 500 ms; or within not more than 400 ms; or within not more than 300 ms; or within not more than 200 ms; or within not more than 190 ms; or within not more than 100 ms. In a specific embodiment, the electronically controlled compressor is capable of establishing the flow rate of from about 4 L/min to about 9 L/min, or from about 4.8 L/min to about 7.2 L/min, or from about 5.5 L/min to about 7.5 L/min, within not more than 500 ms; or within not more than 400 ms; or within not more than 300 ms; or within not more than 200 ms; or within not more than 190 ms; or within not more than 100 ms. In a more specific embodiment, the electronically controlled compressor is capable of establishing the flow rate of about 6 L/min within not more than 500 ms; or within not more than 400 ms; or within not more than 300 ms; or within not more than 200 ms; or within not more than 190 ms; or within not more than 100 ms.

In a further embodiment, the conducting volume of the tubing from the outlet of the electronically controlled compressor to the nebulizer nozzle shall be not more than 20 mL, preferably not more than 14 mL, more preferably not more than 13 mL; for instance, from 7 mL to 13 mL, or from 8 mL to 13 mL, or from 8 mL to 12 mL, or from 9 mL to 12 mL, or from 9 mL to 11 mL, such as 10 mL or 11 mL. For instance, in one specific embodiment, the conducting volume is configured such that the length of the flexible tubing from the outlet of the electronically controlled compressor to the nebulizer nozzle shall be not more than 1400 mm, preferably not more than 1300 mm; for instance, from 1400 mm to 1200 mm, or from 1300 mm to 1100 mm, or from 1200 mm to 800 mm; and the inner diameter of the tubing shall be less than 5 mm; for instance, from 5 mm to 1 mm, or from 4.5 mm to 2 mm, or 4.25 mm to 3 mm, such as 4 mm.

Optionally, dedicated damping means can be placed in the flow path of the compressed air to (further) damp and/or level out air flow oscillations ('compressor noise') generated by the electronically controlled compressor (19). This is depicted, for instance, in FIG. 3B. FIG. 3B is showing one of the preferred embodiments of the inhalation device according to the second aspect of the invention comprising all components of FIG. 3A as described above and in addition a number of optional components, such as a dust- and/or microbial filter (23), air expansion means (24*a*, 24*b*) in front of and behind the electronically controlled compressor (19), a muffler (25) and fixed flow resistance element (27) behind the electronically controlled compressor (19). Said fixed resistance element (27) can be placed directly at the output of the electronically controlled compressor and/or built into the connector (20*a*) for connecting the 'nebulising tube' (21*a*) to the electronically controlled compressor (19).

In cases where more than one electronically controlled compressor is used to provide a flow of gas phase to, and through, the jet nebuliser nozzle, the above provisions shall apply to at least one of them, preferably to all of them.

In one embodiment, the electronically controlled compressor exhibits a nominal operating pressure in the range of about 1.2 bar to about 2.2 bar; or about 1.3 bar to about 2.1 bar; or about 1.4 bar to about 2.0 bar; or about 1.5 bar to about 1.9 bar.

Since the complete gas phase is passing through the jet nebuliser nozzle, these nominal operating pressures are required a) in order to nebulise a liquid pharmaceutical composition, filled into a dedicated fill compartment of the inhalation interface, into an aerosol; and b) in order to provide a desired target flow rate of the gas phase comprising said aerosol (e.g. about 6 L/min) at the downstream end of the jet nebuliser nozzle and to the subject. In a specific embodiment, the electronically controlled compressor exhibits a nominal operating pressure of at least 1.2 bar; or at least 1.3 bar; or at least 1.4 bar; or at least 1.5 bar; or at least 1.6 bar; or at least 1.7 bar; or at least 1.8 bar; for instance, a nominal operating pressure in the range of 1.6 bar to 2.0 bar, such as a nominal operating pressure of 1.8 bar. In a more specific embodiment, the electronically controlled compressor exhibits a nominal operating pressure of at least 1.2 bar; or at least 1.3 bar; or at least 1.4 bar; or at least 1.5 bar; or at least 1.6 bar; or at least 1.7 bar; or at least 1.8 bar; and a nominal flow rate of at least 4 L/min. In a yet more specific embodiment, the electronically controlled compressor exhibits a nominal operating pressure of at least 1.2 bar;

or at least 1.3 bar; or at least 1.4 bar; or at least 1.5 bar; or at least 1.6 bar; or at least 1.7 bar; or at least 1.8 bar; and a nominal flow rate in the range of from about 4 L/min to about 9 L/min, or from about 4.8 L/min to about 7.2 L/min, or from about 5.5 L/min to about 7.5 L/min. In a yet more specific embodiment, the electronically controlled compressor exhibits a nominal operating pressure in the range of 1.6 bar to 2.0 bar, and a nominal flow rate in the range of about 4 L/min to about 9 L/min, or from about 4.8 L/min to about 7.2 L/min, or from about 5.5 L/min to about 7.5 L/min. In one of the preferred embodiments, the electronically controlled compressor exhibits a nominal operating pressure in the range of 1.6 bar to 2.0 bar, and a nominal flow rate of about 6 L/min. In one of the further preferred embodiments, the electronically controlled compressor exhibits a nominal operating pressure of 1.8 bar and a nominal flow rate of about 6 L/min.

In one embodiment of the inhalation device according to the second aspect of the invention, the electronically controlled compressor is a piston compressor. In a specific embodiment, the electronically controlled compressor is equipped with integrated one-way valves to build up the pressure and to allow the pressurised air to exit only through the jet nebuliser nozzle, apart from minor leakages through e.g. sealings between the piston and its surrounding cylinder. This means that the pressurised air is only pumped, or transported, forward in the direction of the jet nebuliser nozzle by the electronically controlled compressor; no air is 'pulled backwards' and away from the jet nebuliser nozzle at any stage, for instance, when the compressor is switched off (e.g. during the exhalation phases). In a further specific embodiment, the electronically controlled compressor is a WOB-L piston compressor (i.e. a unitary piston rod which is mounted to an eccentric bearing assembly and thus 'wobbles' inside the cylinder when the crankshaft, or motor shaft, rotates and which is sealed to the inside of said cylinder by a flanged disk cup). Examples of suitable compressors include, but are by no means limited to, WOB-L compressor models Thomas 8006 and Charles Austen RP12; both models fulfil the requirements for nebulisation flow in terms of flow rate and nebulisation pressure requirements: in this case, for instance, 6 L/min and 1.8 bar.

In one embodiment of the inhalation device according to the second aspect of the invention, the device further comprises one or more user interfaces. Such interfaces are useful in order to enter and/or display, or in other words input and output, use-related information. They can be provided in the form of, for instance, one or more buttons, visual displays, touch displays, and/or data storage media readable at least by the electronic controller of the inhalation device; for instance, so-called smartcards (i.e. cards storing computer-readable data from which said data can be read by a respective reading means e.g. contact based, RFID, NFC). Alternatively, use-related information may be handled via a wireless connection means, such as a radio communication means (e.g. Bluetooth, Near Field Communication NFC, or the like). In a specific embodiment, the user interface is provided in the form of buttons, touch displays and/or smartcards such as to allow the input of treatment specific parameters including drug type, inhalation time, inhalation volume, nebulisation time per treatment session.

Alternatively, or in addition thereto, the user interface is adapted to provide visual, acoustic, and/or tactile feedback to the subject, or patient; e.g. to guide the patient to an inhalation. In one embodiment, the subject, or patient, receives feedback, optionally visual feedback, on parameters such as the pressure at the mouthpiece that is currently used during inhalation; the seconds the patient needs to inhale still to complete the breath; the progress of the treatment session (e.g. as a percentage of treatment time); and/or a meter showing whether the patient inhales within a specific target range of inspiration pressure. In one embodiment, the meter is provided to guide the subject, or patient, to inhale at a conveniently slow flow rate (such as 6 L/min) and to use, or maintain, a positive pressure during inhalation; e.g. a positive pressure support with a specific pre-set target positive pressure. In a specific embodiment, the meter is provided to guide the subject, or patient, to inhale at a conveniently slow flow rate (such as 6 L/min) and to use, or maintain, a pre-set target positive pressure during inhalation, wherein the specific pre-set target positive pressure is 0.5 to 5 mbar; or from 0.5 mbar to 3 mbar, e.g. 2 mbar.

In a specific embodiment, the user interface of the inhalation device may be adapted such as to provide a visual feedback to guide the subject, or patient, through an inhalation with positive pressure support by visualising the target pressure range, the actual pressure at any time during the inhalation, or both; and/or by visualising if the patient is within or outside of the pre-set target pressure range. Optionally, the visual feedback may comprise a light that goes on when the pressure falls outside of the pre-set target pressure range. Further optionally, the visual feedback may comprise a colour-coded feedback; e.g. a green or a red light indicating a pressure within or outside of the pre-set target pressure range, respectively. Further optionally, the visual feedback may comprise a flowmeter such as a rotameter, optionally in form of a digital display, comprising a pointer (such as a 'flag' or 'ball') movably arranged in a visual 'target field' to indicate a pressure within or outside of the pre-set target pressure range by said pointer being positioned inside or outside the visual target field, respectively.

As mentioned above, though, the inventors have found that the majority of neonates, infants and children of not more than 12 years—e.g. from 1 year to 8 years—readily accept the flow rate and inhalation volume provided, or emitted, by the inhalation device, and thus adapt their breathing pattern to it very quickly and intuitively, or in other words 'follow' the flow of gas phase provided. Nonetheless, a visual, acoustic, and/or tactile feedback system may be provided as an additional complementary component to the inhalation device.

In one embodiment of the inhalation device according to the second aspect of the invention, the inhalation device is portable. In a further embodiment, the inhalation device has a weight in the range of from about 0.5 kg to about 3.5 kg; or from about 1.0 kg to about 3.0 kg; or from about 1.5 kg to about 2.5 kg. In a more specific embodiment, the inhalation device is portable, and/or has a weight in the range of from about 0.5 kg to about 3.5 kg.

In one embodiment, the invention according to the second aspect provides an inhalation device adapted to emit an inhalable pharmaceutical composition in the form of an aerosol comprised in a gas phase during the inhalation period of the subject, the inhalation device consisting essentially of:

i. an inhalation interface for providing the emitted aerosol in the gas phase to the airways of a subject, wherein the inhalation interface comprises a mouthpiece and exhibits a static dead volume ($DV_s$) between a nascent aerosol outlet at the upstream end of the inhalation interface and an outlet opening at the downstream end of the inhalation interface facing the subject's mouth of not more than 50 mL (e.g. from 1 mL to 10 mL);

ii. a jet nebuliser associated with the inhalation interface for generating the aerosol, wherein the jet nebuliser operates at a nebulising pressure in the range of 1.6 bar to 2.0 bar, or at a nebulising pressure of 1.8 bar;

iii. a single electronically controlled compressor, optionally a WOB-L compressor, for providing a flow of gas phase to said jet nebuliser, wherein the operation of the electronically controlled compressor is inhalation-triggered by means of a pressure sensor responsive to a suction pressure in, or at, the inhalation interface, wherein the electronically controlled compressor further exhibits a nominal operating pressure of 1.8 bar and a nominal flow rate of 6 L/min, and wherein the electronically controlled compressor is capable of establishing the flow rate within not more than 500 ms;

iv. an electronic controller;

v. a user interface for insertion of a data storage medium readable by the electronic controller, such as a smartcard, to allow the input of treatment specific parameters including drug type, inhalation time, inhalation volume;

vi. a user interface for visually displaying use related information;

wherein the electronic controller is adapted to directly control the operation of the electronically controlled compressor, and wherein the inhalation device is adapted to provide the complete gas phase comprising the aerosol through the nozzle of the jet nebuliser at a constant flow rate of about 6 L/min.

In a further embodiment, the invention according to the second aspect provides an inhalation device adapted to emit an inhalable pharmaceutical composition in the form of an aerosol comprised in a gas phase during the inhalation period of the subject, the inhalation device consisting essentially of:

i. an inhalation interface for providing the emitted aerosol in the gas phase to the airways of a subject, wherein the inhalation interface comprises a facemask and exhibits a static dead volume ($DV_s$) between a nascent aerosol outlet at the upstream end of the inhalation interface and an outlet opening at the downstream end of the inhalation interface facing the subject's mouth of not more than 150 mL (e.g. from 1 mL to 60 mL);

ii. a jet nebuliser associated with the inhalation interface for generating the aerosol, wherein the jet nebuliser operates at a nebulising pressure in the range of 1.6 bar to 2.0 bar, or at a nebulising pressure of 1.8 bar;

iii. a single electronically controlled compressor, optionally a WOB-L compressor, for providing a flow of gas phase to said jet nebuliser, wherein the operation of the electronically controlled compressor is inhalation-triggered by means of a pressure sensor responsive to a suction pressure in, or at, the inhalation interface, wherein the electronically controlled compressor further exhibits a nominal operating pressure of 1.8 bar and a nominal flow rate of 6 L/min, and wherein the electronically controlled compressor is capable of establishing the flow rate within not more than 500 ms;

iv. an electronic controller;

v. a user interface for insertion of a data storage medium readable by the electronic controller, such as a smartcard, to allow the input of treatment specific parameters including drug type, inhalation time, inhalation volume;

vi. a user interface for visually displaying use related information;

wherein the electronic controller is adapted to directly control the operation of the electronically controlled compressor, and wherein the inhalation device is adapted to provide the complete gas phase comprising the aerosol through the nozzle of the jet nebuliser at a constant flow rate of about 6 L/min.

In summary, the inhalation device according to the second aspect of the invention is in particular tailored for neonates, infants and children younger than 12 years, or from 1 to 8 years, a) by providing controlled inhalation volumes and slow flow rates (e.g. 6 L/min) which 'guide' the neonates', infants' or children's inhalation manoeuvres, b) by administering aerosolised drugs, such as budesonide, via inhalation interfaces with minimum static dead volumes ($DV_s$), and c) by being inhalation triggered, or breath-actuated.

The slow flow rate of e.g. 6 L/min allows a more efficient delivery of the aerosol to the small airways; for instance, by avoiding that high percentages of the aerosol are deposited by impaction in the upper airways such as the mouth, throat or nasal cavities, where it could cause undesirable side effects (such as thrush, infections, pneumonia).

The breath-actuation, and in particular breath actuation in combination with keeping a constant flow rate throughout the complete inhalation period, advantageously reduces the virtual dead volume ($DV_v$): once the neonate, infant or child actuates nebulisation by generating a negative pressure (usually, upon onset of inhalation), the system starts to nebulise for a pre-set time (e.g. 2-8 s). After this time, the nebulisation process is switched off again and the aerosol not inhaled keeps standing in the inhalation interface. In other word, the gas phase comprising the aerosol remains mostly stagnant within the inhalation interface and is 'stored' there until the next inhalation is actuated by the neonate, infant or child.

Thereby, the dose that can be administered to the deep lungs is maximised and the required time period to administer a target dose is minimised.

In a third aspect, the invention provides a kit comprising the inhalation device according to the second aspect as described above, together with an inhalable pharmaceutical composition. Optionally, this kit may be intended as a 'starter kit' comprising the inhalation device, a first amount of the inhalable pharmaceutical composition, along with written instructions on the correct use of the inhalation device.

In a fourth aspect, the invention provides the use of the inhalation device according to the second aspect of the invention, or the kit according to the third aspect of the invention in the therapy of a subject suffering from a disease, optionally a pulmonary disease; for instance, in the therapy of a pulmonary disease selected from the group bronchitis, asthma, chronic obstructive pulmonary disease (COPD), pneumonia, cystic fibrosis (CF), idiopathic pulmonary fibrosis (IPF), pulmonary arterial hypertension (PAH), pulmonary alveolar proteinosis (PAP), respiratory distress syndrome (RDS), acute bronchitis, bronchitis, bronchiectasis, primary ciliary dyskinesia, respiratory syncytial virus infection (RSV), chronic cough, or lung cancer.

Further potentially useful embodiments are easily derivable on the basis of the guidance provided herein-above and the following examples.

EXAMPLES

Example 1: Inhalation Volumes in Children Younger than 12 Years

A total of 12 subjects aged 3-5 years and 11 subjects aged 6-11 years was evaluated with regard to the highest inhalation volume they considered comfortable; i.e. which they could inhale slowly and deeply, yet without straining. The results (as summarised below) indicate that the majority of subjects aged 3-5 years can comfortably inhale a volume of up to 0.50 L; the majority of subjects aged 6-11 years can comfortably inhale a volume of up to 0.70 L.

TABLE 2

| Inhalation volume (L) | 3 to 5 years group | 6 to 11 years group |
|---|---|---|
| 0.30 | 1 | 0 |
| 0.40 | 5 | 0 |
| 0.50 | 4 | 0 |
| 0.60 | 1 | 2 |
| 0.70 | 1 | 8 |
| 0.80 | 0 | 1 |

Example 2: In Vitro Deposition Results Conventional Vs. Inventive Inhalation Device in ICRP-66 Human Respiratory Tract Model This in vitro deposition experiment is aimed at comparing the performance of a conventional nebuliser (here a PARI device comprising a VIOS® compressor and a PARI LC Plus nebuliser) with the inhalation device according to the second aspect of the invention (here labelled inventive device) operating at a controlled flow of 6 L/min and an inhalation volume of 0.4 L in the ICRP-66 Human Respiratory Tract Model, using a budesonide suspension product by Astra Zeneca, Pulmicort® respules or similar formulations in high, mid- and low dose strengths of 1 mg/2 mL, 0.5 mg/2 mL and 0.25 mg/2 mL, respectively, as the 'model drug' formulation. Data were calculated for a 4-year-old subject, which is representative for a patient group from 1 to 8 years.

The inventive device used for these test sequences comprised a handset based on PARI LC SPRINT, a jet nebuliser (operating pressure 1.8-2 bar), an electronically controlled compressor for providing a flow of gas phase to said jet nebuliser, and an electronic controller adapted to directly control the operation of the electronically controlled compressor. The inhalation device is adapted to provide the complete gas phase comprising the aerosol through the nozzle of the jet nebuliser.

The 'delivered dose' refers to the dose, or amount of drug which is actually 'leaving' the inhalation device, or is discharged from it, and enters the ICRP-model, or in other words, the dose which—under in vivo conditions—would be made available for actual inhalation by a patient Tables 3 and 4 below lists the results of the in vitro test. As can be seen from the results of this in vitro test, the inventive device achieved far higher percentages of drug deposition in the deep lungs (i.e. the deep lung compartment of the ICRP-model; see "Peripheral deposition of dose delivered"). For the tested inhalation volume of 0.40 L about 36% of the delivered dose reached the deep lungs, versus only about 13% with the conventional nebuliser.

The results also indicate that the delivered dose could be reduced by a factor of about 2.6 while still achieving the same target dose range in the peripheral lungs, or lower lungs, where budesonide and other corticosteroids should preferably be deposited to achieve the best efficacy. For instance, with the 0.5 mg/2 mL strength, the conventional nebuliser provided a delivered dose of ~61 µg of which only ~8.6 µg arrived in the deep lungs while a far larger amount of ~37 µg was deposited in the extrathoracic compartment (which under in vivo conditions could cause both local and systemic side effects).

Using the same 0.5 mg/2 mL strength, the inventive nebuliser provided a delivered dose of only ~23 µg (i.e. 2.6 times less than 61 µg); however, ~7 µg, 8.4 µg or 10.2 µg of said 23 µg arrived in the deep lungs with inhalations volumes of 0.20 L, 0.40 L or 0.80 L, respectively; while only ~10 µg, 9.6 µg or 5.9 µg were deposited in the extrathoracic compartment with inhalations volumes of 0.20 L, 0.40 L or 0.80 L, respectively. This clearly reduces a subject's risk of local and systemic side effects.

Requiring smaller delivered doses to achieve a target deep lung dose also means that the times required to administer a said target dose can be decreased advantageously; and also the amount of pharmaceutical composition needed in excess of this target dose is decreased.

TABLE 3

In vitro deposition data in ICRP deposition model of conventional inhalation devices. Data calculated for a 4-year-old subject, which is representative for a patient group from 1 to 8 years.

| | Filling dose | 1 mg/ 2 mL | 0.5 mg/ 2 mL | 0.25 mg/ 2 mL |
|---|---|---|---|---|
| Conventional nebulizer | Treatment time* | 5 min | 5 min | 5 min |
| | Delivered dose | 117 µg | 52 µg | 26 µg |
| | Extrathoracic deposition of dose delivered | 76.6 µg<br>65.5% | 34.1 µg<br>65.5% | 17.0 µg<br>65.5% |
| | Lung deposition of dose delivered | 29.1 µg<br>24.9% | 13.0 µg<br>24.9% | 6.5 µg<br>24.9% |
| | Peripheral deposition of dose delivered | 15.5 µg<br>13.3% | 6.9 µg<br>13.3% | 3.5 µg<br>3% |

(*Treatment time were captured in clinical trials)

TABLE 4

In vitro deposition data in ICRP deposition model of conventional inhalation devices versus inventive inhalation device. Data calculated for a 4-year-old subject, which is representative for a patient group from 1 to 8 years with a concentration of 0.5 mg of Budesonide per mL and an inhalation volume of 0.4 L

| | | High-dose | Mid-dose | Low-dose |
|---|---|---|---|---|
| Inventive device/ 0.40 L | Treatment time | 3.2 min | 1.6 min | 0.8 min |
| | Delivered dose | 60.0 µg | 30.0 µg | 15.0 µg |
| | Extrathoracic deposition of dose delivered | 14.0 µg<br>41.1% | 9.6 µg<br>41.1% | 4.8 µg<br>41.1% |
| | Lung deposition of dose delivered | 31.8 µg<br>53.0% | 13.0 µg<br>53.0% | 7.9 µg<br>53.0% |
| | Peripheral deposition of dose delivered | 21.7 µg<br>36.2% | 10.9 µg<br>36.2% | 5.4 µg<br>36.2% |

The invention claimed is:

1. A method of treatment of a subject being a neonate, infant, or child younger than 12 years suffering from asthma, the method comprising administering to said subject a composition suitable for treating asthma as an aerosol via a mouthpiece, wherein said aerosol is comprised in a gas phase, and wherein said gas phase is administered to said subject:

(a) at a flow rate of from about 4 L/min to about 9 L/min during the inhalation period of the subject, (b) at a total volume of about 0.10 L to about 0.80 L per inhalation, and (c) wherein the gas phase comprising the aerosol is administered via an inhalation interface exhibiting a static dead volume (DVs) between a nascent aerosol outlet at the upstream end of the inhalation interface and an outlet opening at the downstream end of the inhalation interface facing the subject's mouth in the range of from about 1 mL to about 10 mL.

2. The method according to claim 1, wherein the gas phase comprising the aerosol is generated by an inhalation device adapted to:

(aa) emit the gas phase comprising the aerosol during the inhalation period of the subject at a flow rate of from about 4 L/min to about 9 L/min, and (bb) emit, per inhalation, a total volume of about 0.10 L to about 0.80 L of the gas phase.

3. The method according to claim 1, wherein the gas phase comprising the aerosol is administered during the inhalation period of the subject at a flow rate in the range of from about 4.8 L/min to about 7.2 L/min, and at a total volume of the gas phase in the range of from about 0.40 L to about 0.80 L.

4. The method according to claim 1, wherein the gas phase comprising the aerosol is administered via the inhalation interface comprising a mouthpiece or a facemask.

5. The method according to claim 1, wherein the gas phase comprising the aerosol is administered via the inhalation interface being a mouthpiece or a facemask at an overpressure of up to about 10 mbar.

6. The method according to claim 1, wherein the inhalation device comprises a jet nebuliser, a vibrating mesh nebuliser or a spray nozzle nebuliser.

7. The method according to claim 1, wherein the aerosol generator comprises a jet nebuliser operating at a nebulising pressure in the range of 1.6 bar to 2.0 bar.

8. The method according to claim 1, wherein the composition comprises a glucocorticoid selected from budesonide, fluticasone propionate, beclomethasone dipropionate, ciclesonide, flunisolide, mometasone furoate, and triamcinolone acetonide.

* * * * *